(12) United States Patent
Joseph et al.

(10) Patent No.: US 8,052,926 B2
(45) Date of Patent: Nov. 8, 2011

(54) METHOD FOR MANUFACTURING A STERILIZED LANCET INTEGRATED BIOSENSOR

(75) Inventors: Abner David Joseph, Carmel, IN (US); Frank A. Chan, Sunnyvale, CA (US); Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 631 days.

(21) Appl. No.: 12/180,101

(22) Filed: Jul. 25, 2008

(65) Prior Publication Data

US 2009/0010802 A1   Jan. 8, 2009

Related U.S. Application Data

(60) Continuation-in-part of application No. 11/070,502, filed on Mar. 2, 2005, now Pat. No. 7,815,579, and a continuation-in-part of application No. 11/326,422, filed on Jan. 5, 2006, now Pat. No. 7,481,777, and a continuation-in-part of application No. 12/038,302, filed on Feb. 27, 2008, now Pat. No. 7,976,477, which is a division of application No. 10/330,724, filed on Dec. 27, 2002, now abandoned.

(51) Int. Cl.
*A61L 2/00* (2006.01)
*H01J 27/00* (2006.01)
*G01N 23/00* (2006.01)
*A61N 5/00* (2006.01)
*A61B 10/00* (2006.01)
*A61B 5/00* (2006.01)
*B65B 55/02* (2006.01)
*B65B 9/00* (2006.01)
*B65B 51/10* (2006.01)

(52) U.S. Cl. ............ 422/22; 422/1; 422/24; 422/50; 422/410; 422/430; 250/427; 250/432 R; 250/455.11; 250/492.1; 600/583; 600/584; 600/566; 600/567; 53/425; 53/450; 53/477

(58) Field of Classification Search ............ 422/1, 22, 422/24, 50, 410, 430; 250/427, 432 R, 455.11, 250/492.1; 600/583–584, 566–567; 53/425, 53/450, 477
See application file for complete search history.

(56) References Cited

U.S. PATENT DOCUMENTS 2,931,903 A * 4/1960 Van De Graaff et al. ..... 250/398
(Continued)

FOREIGN PATENT DOCUMENTS

DE            28 03 345 B1      6/1969
(Continued)

OTHER PUBLICATIONS

International Patent Application No. PCT/EP2009/005309 International Search Report and Written Opinion mailed Jan. 26, 2010.

*Primary Examiner* — Jill Warden
*Assistant Examiner* — Monzer Chorbaji
(74) *Attorney, Agent, or Firm* — Woodard, Emhardt, Moriarty, McNett & Henry LLP

(57) ABSTRACT

An integrated disposable includes a test strip and a lancet packet coupled to the test strip. The lancet packet includes a sterility sheet enclosing at least a portion of a lancet to maintain the sterility of the lancet. The lancet packet and the sterility sheet, in particular, allow the lancet to be sterilized separately from the test strip. The lancet in one form is incorporated into a lancet tape that is sterilized in a continuous, reel-to-reel sterilization process. The lancet tape in one form is sterilized using an electron beam sterilization process. With electron beam sterilization, sterilization is enhanced by irradiating both sides of the tape with electron beams. Sterilization can adversely affect chemical reagents in the test strip. To alleviate this chemistry degradation issue, the lancet packet is attached to the test strip after the lancet is sterilized.

33 Claims, 13 Drawing Sheets

U.S. PATENT DOCUMENTS

| | | | |
|---|---|---|---|
| 3,833,814 A | 9/1974 | Nablo | |
| 4,635,633 A | 1/1987 | Hufnagle | |
| 4,787,398 A | 11/1988 | Garcia et al. | |
| 4,994,068 A | 2/1991 | Hufnagle | |
| 5,396,074 A | 3/1995 | Peck et al. | |
| 5,692,610 A * | 12/1997 | Porteous | 206/388 |
| 6,140,657 A | 10/2000 | Wakalopulos et al. | |
| 6,315,738 B1 | 11/2001 | Nishikawa et al. | |
| 6,360,888 B1 | 3/2002 | McIvor et al. | |
| 6,520,326 B2 | 2/2003 | McIvor et al. | |
| 6,561,989 B2 | 5/2003 | Whitson | |
| 6,591,125 B1 | 7/2003 | Buse et al. | |
| 6,594,156 B1 | 7/2003 | Van Antwerp et al. | |
| 6,608,882 B2 | 8/2003 | Allen et al. | |
| 6,612,111 B1 | 9/2003 | Hodges et al. | |
| 6,653,641 B2 | 11/2003 | Lyons et al. | |
| 6,685,883 B2 | 2/2004 | Schianchi et al. | |
| 6,833,551 B2 | 12/2004 | Avnery | |
| 6,866,675 B2 | 3/2005 | Perez et al. | |
| 6,945,017 B1 * | 9/2005 | Bonney et al. | 53/477 |
| 6,988,996 B2 | 1/2006 | Roe et al. | |
| 7,396,334 B2 * | 7/2008 | Kuhr et al. | 600/583 |
| 2002/0023852 A1 | 2/2002 | Mcivor et al. | |
| 2002/0057987 A1 | 5/2002 | Loda et al. | |
| 2002/0149321 A1 | 10/2002 | Avnery | |
| 2002/0168290 A1 | 11/2002 | Yuzhakov et al. | |
| 2003/0050573 A1 | 3/2003 | Kuhr et al. | |
| 2003/0083685 A1 | 5/2003 | Freeman et al. | |
| 2003/0094384 A1 | 5/2003 | Vreeke et al. | |
| 2003/0143113 A2 | 7/2003 | Yuzhakov et al. | |
| 2003/0144608 A1 | 7/2003 | Kojima et al. | |
| 2003/0199893 A1 | 10/2003 | Boecker et al. | |
| 2003/0211619 A1 | 11/2003 | Olson et al. | |
| 2004/0049220 A1 | 3/2004 | Boecker et al. | |
| 2004/0060260 A1 | 4/2004 | Gottlieb et al. | |
| 2004/0064068 A1 | 4/2004 | DeNuzzio et al. | |
| 2004/0106941 A1 | 6/2004 | Roe et al. | |
| 2004/0120848 A1 | 6/2004 | Teodorczyk | |
| 2004/0127818 A1 | 7/2004 | Roe et al. | |
| 2004/0127819 A1 | 7/2004 | Roe | |
| 2004/0163987 A1 | 8/2004 | Allen | |
| 2004/0186394 A1 | 9/2004 | Roe et al. | |
| 2004/0193202 A1 | 9/2004 | Allen | |
| 2004/0206636 A1 | 10/2004 | Hodges et al. | |
| 2005/0036909 A1 | 2/2005 | Erickson et al. | |
| 2005/0133729 A1 | 6/2005 | Woodworth et al. | |
| 2005/0139489 A1 | 6/2005 | Davies et al. | |
| 2005/0158205 A1 | 7/2005 | Swanson et al. | |
| 2005/0245954 A1 | 11/2005 | Roe et al. | |
| 2005/0251064 A1 | 11/2005 | Roe | |
| 2005/0277850 A1 | 12/2005 | Mace et al. | |
| 2005/0283094 A1 | 12/2005 | Thym et al. | |
| 2006/0008389 A1 | 1/2006 | Sacherer et al. | |
| 2006/0079810 A1 | 4/2006 | Patel et al. | |
| 2006/0100542 A9 | 5/2006 | Wong et al. | |
| 2006/0100543 A1 | 5/2006 | Raney et al. | |
| 2006/0174592 A1 | 8/2006 | Chan | |
| 2006/0200045 A1 | 9/2006 | Roe | |
| 2006/0216817 A1 | 9/2006 | Hoenes et al. | |
| 2006/0229532 A1 | 10/2006 | Wong et al. | |
| 2006/0247555 A1 | 11/2006 | Harttig | |
| 2007/0016103 A1 | 1/2007 | Calasso et al. | |
| 2007/0167869 A1 | 7/2007 | Roe | |
| 2007/0173740 A1 | 7/2007 | Chan et al. | |
| 2007/0176120 A1 | 8/2007 | Schwind et al. | |
| 2008/0103415 A1 | 5/2008 | Roe et al. | |
| 2008/0147107 A1 | 6/2008 | Roe et al. | |

FOREIGN PATENT DOCUMENTS

| | | |
|---|---|---|
| EP | 0 199 484 B1 | 10/1986 |
| EP | 1 232 760 A1 | 8/2002 |
| EP | 1 714 613 A1 | 10/2006 |
| JP | H10-005198 | 1/1998 |
| WO | WO 03/077957 A1 | 9/2003 |
| WO | WO 2006/092281 A2 | 9/2006 |
| WO | WO 2007/077212 A1 | 7/2007 |

* cited by examiner

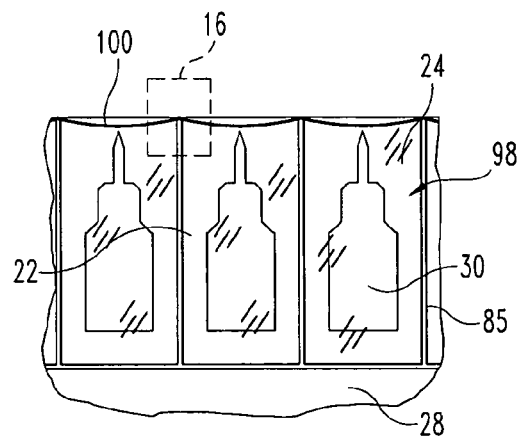
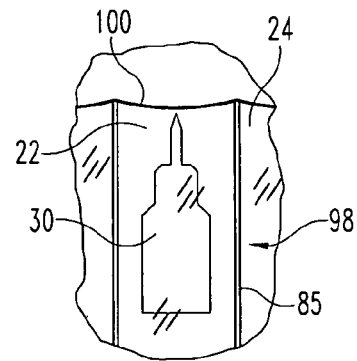
Fig. 14  Fig. 15
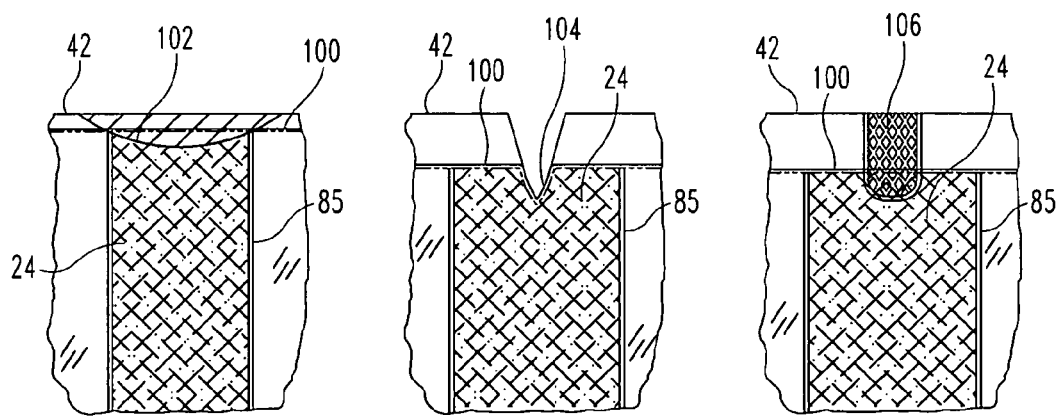
Fig. 16  Fig. 17  Fig. 18

1 Sided Irradiation - 150 k$_e$V

2 Sided Irradiation - 150 k$_e$V

METHOD FOR MANUFACTURING A STERILIZED LANCET INTEGRATED BIOSENSOR

CROSS REFERENCE TO RELATED APPLICATIONS

This application is a continuation-in-part of U.S. patent application Ser. No. 11/070,502, filed Mar. 2, 2005 now U.S. Pat. No. 7,815,579, which is hereby incorporated by reference in its entirety. This application is a continuation-in-part of U.S. patent application Ser. No. 11/326,422, filed Jan. 5, 2006 now U.S. Pat. No. 7,481,777, which is hereby incorporated by reference in its entirety. This application is a continuation-in-part of U.S. patent application Ser. No. 12/038,302, filed Feb. 27, 2008 now U.S. Pat. No. 7,976,477, which is a divisional of U.S. patent application Ser. No. 10/330,724, filed Dec. 27, 2002 now abandoned, which are hereby incorporated by reference in their entirety.

BACKGROUND

The present invention generally relates to bodily fluid sampling devices and more specifically, but not exclusively, concerns a technique for mass-producing integrated disposables.

The acquisition and testing of bodily fluids is useful for many purposes and continues to grow in importance for use in medical diagnosis and treatment, such as for diabetes and in other diverse applications. In the medical field, it is desirable for lay operators to perform tests routinely, quickly, and reproducibly outside of a laboratory setting with rapid results and a readout of the resulting test information. Testing can be performed on various bodily fluids and, for certain applications, is particularly related to the testing of blood and/or interstitial fluid.

Recently, integrated disposables, such as lancet integrated test strips and microsamplers, have been developed in which a test strip is integrated with a lancet so as to form a single disposable unit. The term "disposable" commonly refers to components, such as test strips and lancets, that are typically used once for a test and then discarded or disposed of afterwards, which contrasts with other more permanent (and expensive) components, like meters and firing mechanisms, that are repeatedly used for multiple tests. Lancets are usually discarded after use because lancets are contaminated with blood or other biological fluids that can create a biohazard. Likewise, test strips are discarded after a single use due to blood contamination during testing. Additionally, given that the reagents used for testing are consumed during analysis, test strips by their very nature can usually perform a single accurate test. Integrated disposables typically combine the functions of a test strip with a lancet or a needle to form a single disposable unit.

While these integrated disposables have somewhat simplified the collection and testing of fluid samples, there are still a number of issues that need to be resolved before a successful commercial unit can be implemented. Considering that integrated disposables are only used once and then discarded after each test and typically multiple tests are conducted in a day, the disposables need to be inexpensive and must be able to be produced in high volumes to satisfy consumer demand. A related issue concerns sterilizing and maintaining the sterility of the lancet so as to minimize the risk of infection. In practice, conventional plastic or syringe-type caps that are used to maintain the sterility of typical lancets cannot be incorporated with integrated disposables for several reasons, especially for those designs with lancets that are moveable relative to the rest of the test strip. With typical syringe-type caps, the cap encapsulates the lancet, and the cap is removed by pulling or twisting the cap off the lancet. However, the removal of the cap from the lancet without destroying or damaging the integrated disposable is difficult or even practically impossible. Moreover, automatic cap removal with such caps can be difficult.

Integrated disposables have been proposed in which the lancet is encapsulated within a sterilized plastic body or a molded plastic plug that encloses one end of a lancet chamber. During lancing, the lancet pierces the body so as to extend from the body and lance the tissue. Such a design is suitable for automated systems because the lancet can be fired without the need to remove a protective cap. Given their bulky and rigid nature, these types of designs are not well suited for magazines, drums, cassettes, cartridges, and the like, however. The encapsulating plastic also creates a rather large profile which does not allow a plurality of integrated devices to be packed in a tight package. Moreover, the injection molding required to manufacture these types of integrated devices can make the devices considerably more expensive as well as more difficult to assemble. Such designs can also limit how small the lancet can be because the lancet has to be rigid enough to still be able to puncture the seal.

Other integrated disposable designs have been proposed in which the entire unit is sealed within a protective packet. However, these designs require the entire disposable unit to be sterilized at the same time, which results in a whole host of difficulties. Unfortunately, sterilization techniques for lancets, such as radiation, adversely affect the chemical enzymes of the test strip. Hence, if left uncompensated, the accuracy of the test strip can be significantly hampered. Moreover, certain desirable sterilization techniques for lancets are impractical when the lancet and test strip are combined together because these techniques tend to damage or even destroy components on the test strip. In addition, undesirable cross contamination can occur between the lancet and the test strip when sealed in the same protective packet. For instance, components of the test strip, such as chemicals, biological components, adhesives, and the like, can migrate within the packet onto the lancet, thereby possibly compromising the sterility of the lancet.

Thus, needs remain for further contributions in this area of technology.

SUMMARY

One aspect concerns a method in which a web of lancets are sealed within a sterility sheet. The lancets are sterilized. After sterilizing the lancets, the web of the lancets are joined with a belt that has a plurality of biosensors to create a tape of integrated disposables. In other embodiments, lancet packets are singulated from the web of lancets and are individually joined with a corresponding biosensor on the belt.

Another aspect concerns a method in which a lancet packet tape is created by sealing a plurality of lancet assemblies within a sterility sheet. A seal is formed between each of the assemblies to form individualized lancet packets. The lancet packet tape is attached to a biosensor tape that includes a plurality of biosensors.

A further aspect concerns a method in which a lancet tape that has a plurality of lancet assemblies is provided. The lancet tape has opposing first and second sides. The lancet tape is sterilized with an electron beam sterilization system. The first side of the lancet tape is irradiated with one or more first electron beams. The second side of the lancet tape is irradiated with one or more second electron beams. In one embodiment, the lancet tape is provided to the sterilization system in a reel-to-reel process.

Further forms, objects, features, aspects, benefits, advantages, and embodiments of the present invention will become apparent from a detailed description and drawings provided herewith.

BRIEF DESCRIPTION OF THE DRAWINGS

FIG. 14 is a top view of a lancet packet tape in which the lancets are packaged without a guide member.

FIG. 15 is an enlarged view of an individual lancet packet in the lancet packet tape of FIG. 14.

FIG. 16 is a top view of scalloped-shaped end seal pattern for a lancet packet.

FIG. 17 is a top view of a notched end seal pattern.

FIG. 18 is a top view of an end seal pattern that includes a grid patch.

DESCRIPTION OF THE SELECTED EMBODIMENTS

Figure 1:
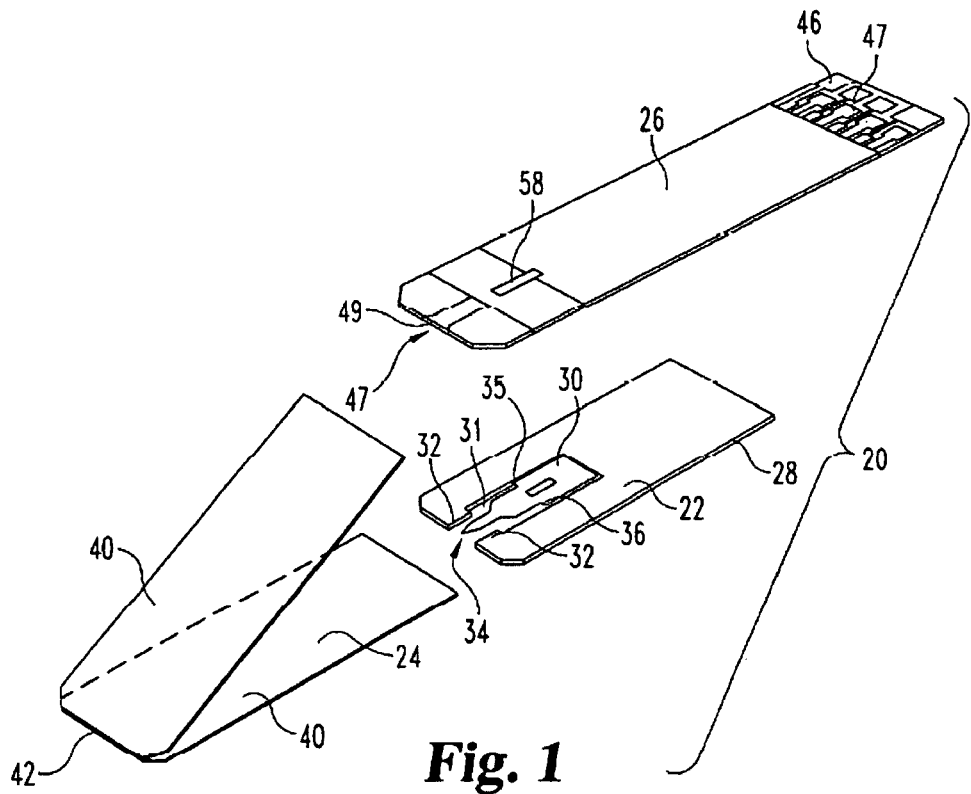
FIG. 1 is a first top exploded view of an integrated disposable according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in detail, although it will be apparent to those skilled in the relevant art that some features that are not relevant to the present invention may not be shown for the sake of clarity. It should be noted that directional terms, such as "left", "right", "top", "bottom", "clockwise" and "counterclockwise", are used herein solely for the convenience of the reader in order to aid in the reader's understanding of the illustrated embodiments, and it is not the intent that the use of these directional terms in any manner limit the described, illustrated, and/or claimed features to a specific direction or orientation.

One embodiment of the present invention concerns a unique technique for mass-producing an integrated single use disposable for biological fluid testing, such as for blood glucose testing. The integrated disposable includes a lancet for forming an incision that is attached to a test strip for analyzing fluid from the incision. The lancet is at least partially (or entirely) enclosed by a sterility sheet or barrier, which maintains sterility of the lancet and simplifies manufacturing of the integrated disposable. By enclosing the lancet in the sterility sheet, the lancet can be sterilized separately from the test strip and then attached to the test strip after sterilization. As a result, this separate or modular construction of lancet and test strip allows the lancet to be sterilized without adversely affecting chemical enzymes or other chemistry in the test strip that would affect the accuracy of the test results. In one process for sterilizing the lancet, the lancet enclosed by the sterility sheet is irradiated on two opposing sides by electron beams, which has been found to be a quite effective method for sterilizing the lancet in high volume production. The sterility sheet also minimizes cross-contamination between the lancet and the test strip before, during, and after use. In one form, the integrated lancing test strip is loaded into a lancing device or meter that is configured to fire the lancet. The lancet is exposed for use by removing, separating, slitting, and/or piercing the sterility sheet. The sterility sheet can also be reinforced by a seal or membrane on a cartridge or dispenser in which one or more integrated disposables are stored.

A lancet integrated test strip (LIT) or integrated disposable 20 that is manufactured via a technique according to one embodiment, among many, of the present invention will be described initially with reference to FIGS. 1, 2, 3, and 4. Referring to FIG. 1, the LIT 20 includes a lancet assembly/packet or incision forming assembly 22 for forming an incision in tissue, a sterility sheet or cover foil 24 for maintaining the sterility of the lancet assembly 22, and a test strip or biosensor 26 for acquiring a body fluid from the incision. Both the lancet assembly 22 and the test strip 26 in the illustrated embodiment are generally flat such that the LIT 20 has an overall flat appearance. It should nonetheless be recognized that the lancet assembly 22 and the LIT 20 as well as other components can have a different overall shape. For some nonlimiting examples of other types of integrated disposables that can be manufactured via the below described technique, please refer to U.S. Patent Application Publication Nos. 2004/0127818 A1, 2006/0079810 A1, and 2006/0229532 A1, which are hereby incorporated by reference. In the illustrated embodiment, the lancet assembly 22 is secured to the test strip 26 in a dynamic manner; that is, the lancet assembly 22 is able to move relative to the test strip 26. Nevertheless, it should be appreciated that in other embodiments the lancet assembly 22 or certain portions thereof (such as a guide member 28) can be fixed relative to the test strip 26. For example, as will be described below, the guide member 28 may be secured within a lancet packet 44 by sealing sterility sheet 24 to the guide member 28, leaving a lancet 30 dynamically disposed within the lancet assembly 22.

As can be seen in the embodiment of FIG. 1, the lancet assembly 22 has a spacer or guide member 28 that guides the piercing member or lancet 30 during lancing. In one form, the guide member 28 has an appropriate thickness to allow the lancet 30 to move within a guide slot 31 while the lancet assembly 22 is packaged within the sterility sheet 24. The lancet 30 is slidably retained within a guide slot or opening 31 that is defined in the guide member 28. In the course of lancing, the guide slot 31 guides the movement of the lancet 30 during both extension and retraction. In the illustrated embodiment, the lancet 30 and the guide member 28 are separate components that are not directly attached to one another. Nevertheless, in other embodiments (not shown), the lancet 30 and the guide member 28 can be connected to one another. For example, the lancet assembly 22 can have breakable tabs that connect the lancet 30 to the guide member 28 so that the lancet 30 is held in place during manufacturing as well as prior to lancing, thereby reducing the risk of injury. During lancing, the tabs are broken to allow the lancet 30 to extend from the integrated lancing test strip 20. In another example, a spring for retracting the lancet 30 connects the guide member 28 to the lancet 30. It is envisioned that the guide member 28 is optional in other embodiments.

In the embodiment shown, end stops 32 of the guide member 28 extend inwardly at a slot opening 34 of the guide slot 31 so as to limit the movement of the lancet 30, thereby retaining the lancet 30 in the guide slot 31. The lancet 30 has a body portion 35 with one or more stop edges 36, which are wider than the slot opening 34. When the lancet 30 is fully extended, the stop edges 36 of the lancet 30 can contact the end stops 32, and thus limit the travel of the lancet 30. However, in other embodiments, a firing mechanism, which is used to fire the lancet 30, limits the travel of the lancet 30. A neck portion 37 of the lancet 30, which is slightly smaller than the size of the slot opening 34, extends from the body portion 35 of the lancet 30. During extension of the lancet 30, the neck 37 is received between the end stops 32 such that the end stops 32 can limit undesirable rotation of the lancet 30 as the tissue is punctured. Extending from the neck 37, the lancet 30 has a blade portion or tip 38 that is configured to cut tissue. In the illustrated embodiment, the lancet 30 defines an engagement notch 39 for coupling the lancet 30 to a firing mechanism (not shown).

Figure 2:
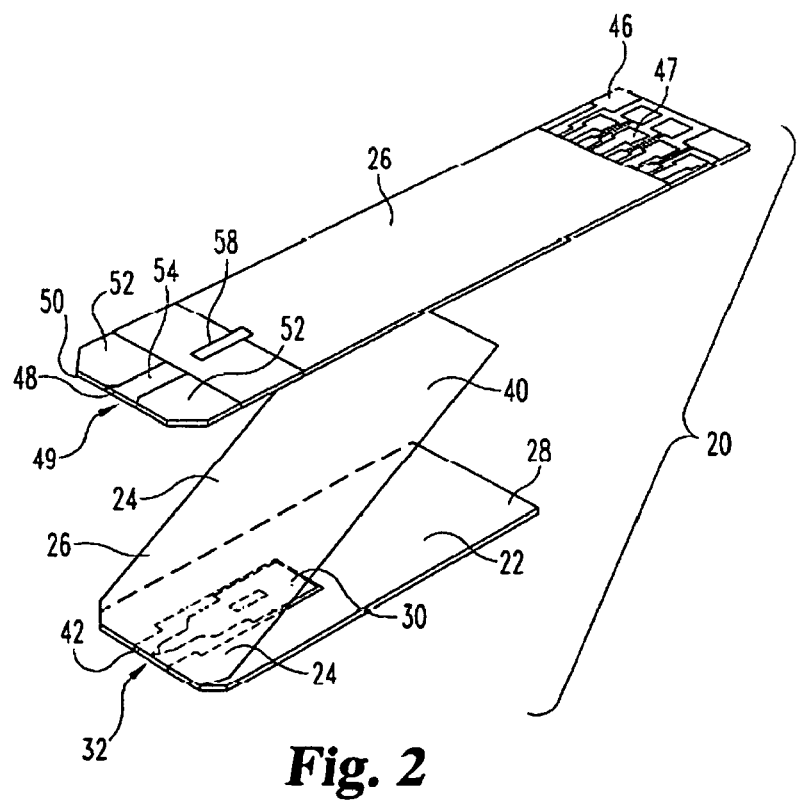
FIG. 2 is a second top exploded view of the FIG. 1 integrated disposable.
Figure 3:
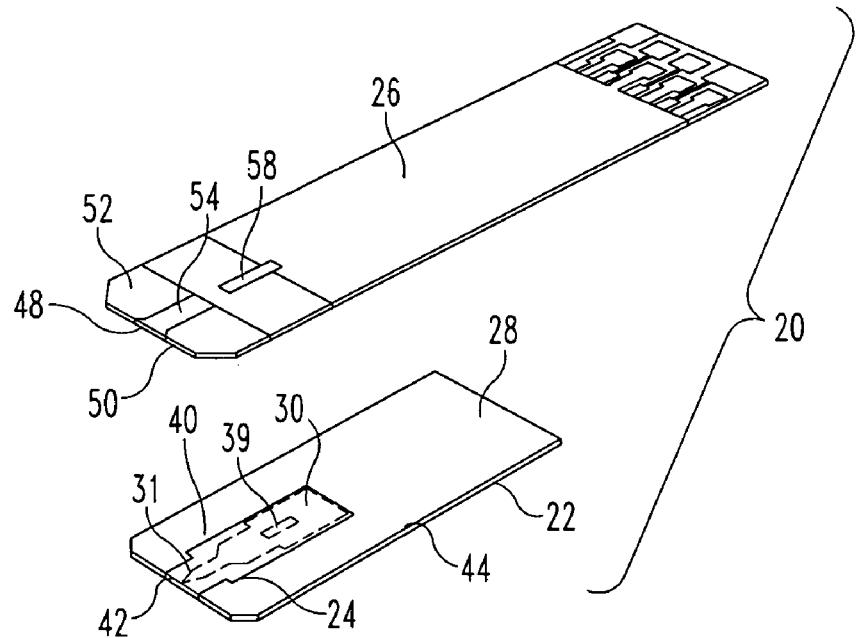
FIG. 3 is a third top exploded view of the FIG. 1 integrated disposable.

Referring to FIGS. 1 and 2, the lancet assembly 22 is sandwiched between two fold sections or flaps 40 of the sterility sheet 24. A crease 42 between the two flaps 40 closes the slot opening 34 of the guide slot 31. As depicted in FIG. 3, the flaps 40 are secured to the opposite (flat) sides of the lancet assembly 22 so that the lancet 30 is sealed inside the guide slot 31 with the slot opening 34 closed by the crease 42. Once joined together, the lancet assembly 22 and the sterility sheet 24 form a lancet packet 44. With the lancet packet 44, sterilization of the lancet assembly 22 can occur separately without exposing the test strip to the undesirable affects of lancet sterilization. Consequently, the lot specific calibration data can be generated before the lancet packet 44 is attached to the test strip 26.

In the illustrated embodiment, the test strip 26 is an electrochemical type test strip. In one particular form, the test strip 26 includes a modified version of an AVIVA® ACCU-CHEK® brand test strip (Roche Diagnostics Operations, Inc.), but it is envisioned that other types of test strips can be used. For example, the test strip 26 in other embodiments can include an optical type test strip or can analyze fluid samples in other manners. At one end, the test strip 26 in the illustrated embodiment includes a connection portion 46 with electrical contacts 47 that transmit sample readings to a meter. Opposite the connection portion 46, the test strip 26 has a capillary channel 48 with a capillary opening 49 that is configured to draw a body fluid sample from an incision formed by the lancet 30 via capillary action. In the illustrated embodiment, the test strip 26 has a base or substrate 50, one or more spacers 52, and a cover film 54 that together define the capillary channel 48. In one embodiment, the cover film 54 is transparent or semi-transparent so that the user can view the fill sufficiency of the capillary channel 48, but in other embodiments, the cover film 54 or portions thereof can be opaque or semi-opaque. Inside, the capillary channel 48 of the test strip 26 has an analysis region that includes electrodes disposed on the substrate 50, such as working, counter, and/or reference electrodes, and reagents for analyzing the fluid sample. In one form, the connection portion 46 is connected to a meter, and the sample readings from the electrodes in the analysis region are transmitted to the meter via the electrical contacts 47.

Figure 5:
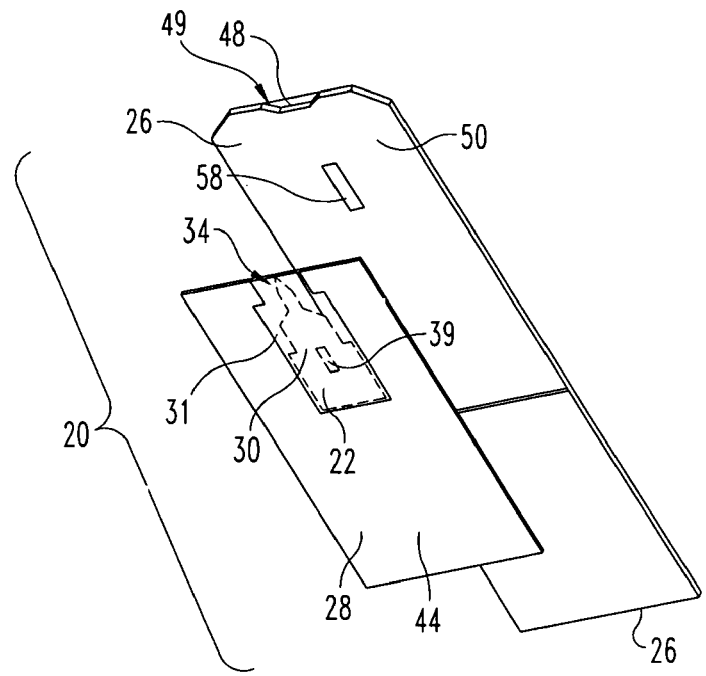
FIG. 5 is a bottom exploded view of the FIG. 1 integrated disposable.
Figure 6:
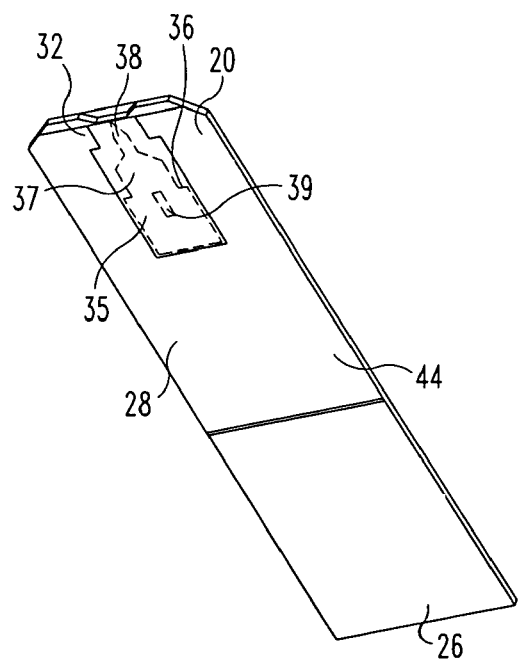
FIG. 6 is a bottom perspective view of the FIG. 1 integrated disposable.

Looking at FIGS. 5 and 6, the sterilized lancet packet 44 is attached to the test strip 26 to form the LIT 20. As depicted, the lancet packet 44 is attached at the end of the test strip 26 proximal to the capillary opening 49 of the capillary channel 48. In particular, the guide slot opening 34 of the lancet assembly 22 and the capillary opening 49 of the test strip 26 are positioned near one another in a side-by-side relationship so that when the lancet 30 forms the incision, the capillary channel opening 49 is positioned in close proximity to collect the body fluid. The test strip 26 is attached to the exterior of the sterility sheet 24 enclosing the lancing member 22 to complete the LIT 20. The test strip 26 in one form is attached to the lancet packet 44 through an adhesive, but as will be explained below, the test strip 26 and lancet packet 44 can be attached in other manners. In one form, the lancet packet 44 is attached to the test strip 26 such that the end edges of both are aligned with one another. However, in other embodiments the edges of the lancet packet 44 and the test strip 26 can be offset from one another. For example, the edge of the lancet packet 44 in the illustrated embodiment, as is demarked by crease 42, is recessed slightly from the edge of the test strip 26 at the capillary opening 49. By having the lancet packet 44 recessed, fluid flow to the capillary channel opening 49 is promoted. In another example, the sterility sheet 24 is positioned such that the crease 42 extends past the edge of the test strip 26. With this example, all or part of the sterility sheet 24 can be hydrophobic and/or hydrophilic so as to direct fluid flow towards the capillary channel 48. In one particular form, the sterility sheet 24 extends from the test strip 26 such that the sterility sheet 24 acts like a flexible wicking flag that draws fluid into the capillary channel 48.

In order to enhance fluid flow towards the capillary channel opening 49, the sterility sheet 24 can be treated and/or made to be hydrophobic. With the sterility sheet 24 being hydrophobic, the sterility sheet 24 can squeegee or wipe body fluid from the lancet 30 as the lancet 30 retracts back inside the guide slot 31. It is thought that the wiping action of the sterility sheet 24 increases the amount of body fluid available for sampling as well as makes the lancet 30 cleaner for disposal purposes. As noted before, with the lancet 30 sealed in the lancet packet 44, the risk of cross-contamination between the lancet 30 and the test strip 26 is reduced.

The test strip 26 further defines a relief slot 58 through which a blade tip of a firing arm extends when engaging the lancet 30 during loading and firing. In addition, the relief slot 58 can be used to vent air from the capillary channel 48 as fluid is collected. The length of the relief slot 58 generally approximates the length of the lancing stroke of the firing mechanism used to actuate the lancet 30. When the lancet packet 44 is attached to the test strip 26, the engagement notch 39 on the lancet 30 is aligned with the relief slot 58 in the test strip 26. The blade tip of the firing arm extends through the engagement notch 39 of the lancet 30 as well as into the relief slot 58. When doing so, the blade tip pierces the sterility sheet 24.

Figure 4:
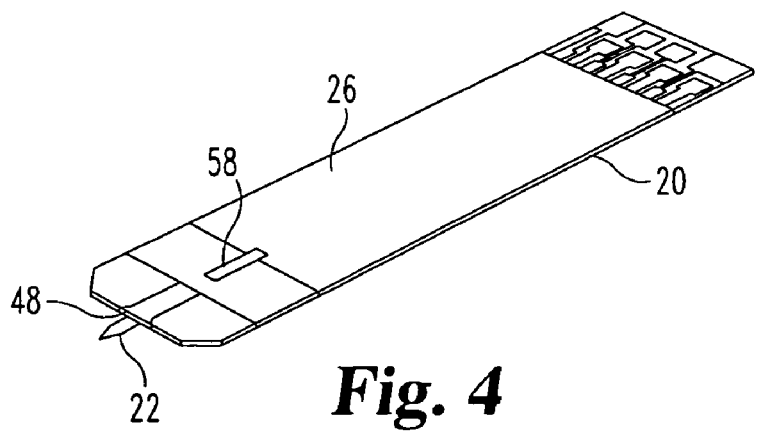
FIG. 4 is a top perspective view of the FIG. 1 integrated disposable with its lancet in an extended position.
Figure 7:
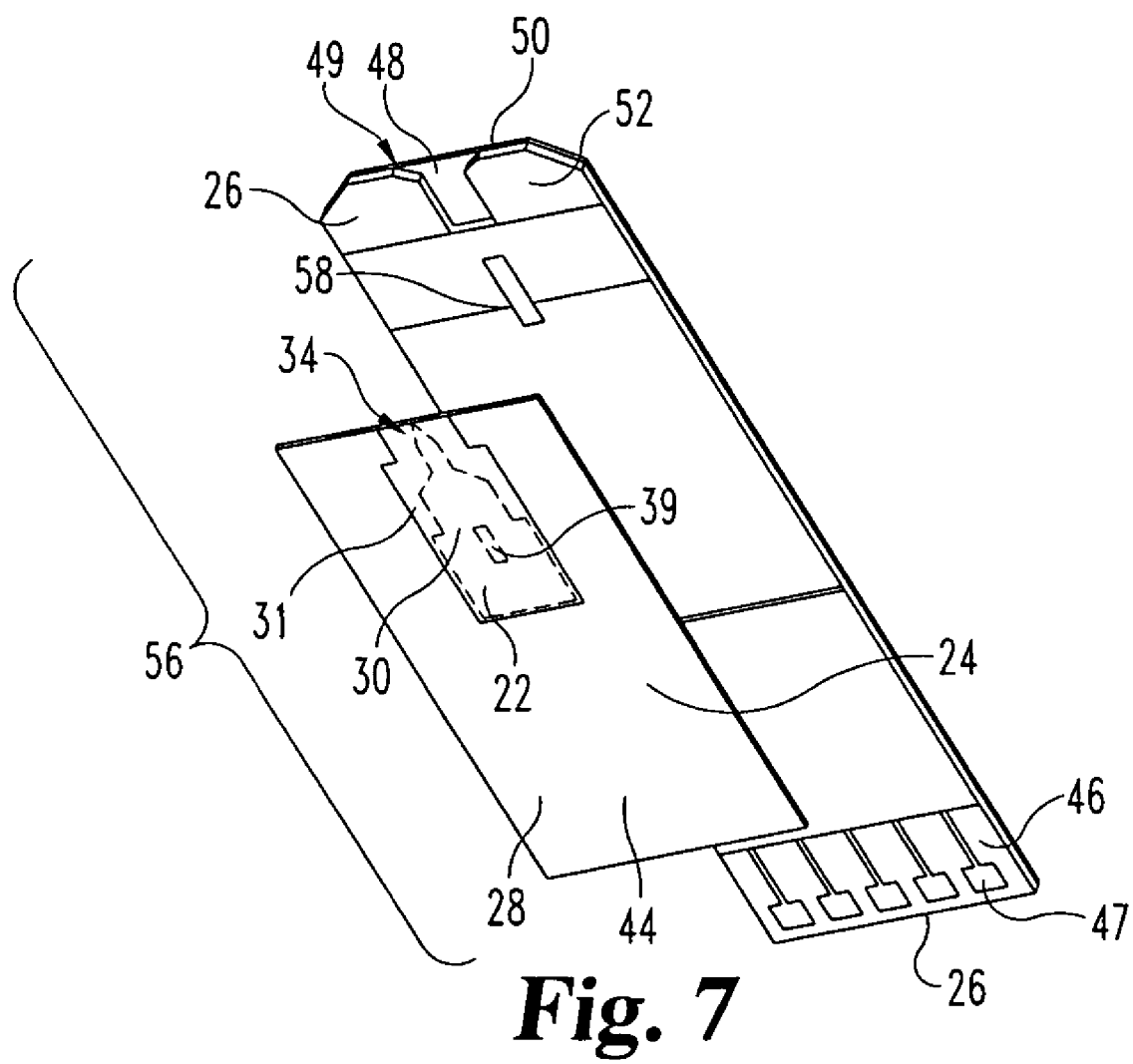
FIG. 7 is an exploded view of an integrated disposable according to another embodiment.

During lancing, the firing arm via the blade extends and retracts the lancet 30 relative to the test strip 26. As the lancet 30 extends, the tip 38 of the lancet 30 pierces the sterility sheet 24 at crease 42, as is illustrated in FIGS. 4 and 7. In one form, the sterility sheet 24 at the crease 42 is weakened so as to aid in puncturing by the lancet 30, but in other forms, the crease 42 is not weakened. Once the lancet 30 is retracted back inside the guide slot 31, as is shown in FIG. 6, the two flaps 40 of the sterility sheet 24 can hold the lancet 30 inside through friction. By engaging the lancet 30 in such a manner, the risk of accidental puncturing by the integrated lancing test strip 26 is reduced because it is more difficult to manually and/or accidentally actuate the lancet 30. It should be recognized that the lancet assembly 22 can incorporate other structures for engaging the lancet 30. For instance, the engagement notch 39 in the lancet 30 can be replaced with a protrusion or knob. It is also contemplated that the lancet can be fired through non-mechanical and/or non-contact techniques, which do not require the puncturing of the sterility sheet 24. As an example, the lancet 30 in another embodiment is magnetized and fired magnetically through a voice coil driver. With the lancet 30 enclosed in the sterility sheet 24 both before and after lancing, the risk of contamination is reduced, and the risk of accidental injury is likewise reduced.

In the embodiment depicted in FIG. 5, the lancet packet 44 is attached to the side of the test strip 26 that has the base 50. It should be appreciated that the lancet packet 44 can be attached to the other side of the test strip 26 as well. For example, in an LIT 56 according to another embodiment, which is illustrated in FIG. 7, the lancet packet 44 is attached to the side that is opposite the base 50. In the depicted embodiment, the cover film 54 over the capillary channel 48 has been eliminated, and the sterility sheet 24 of the lancet packet 44 substitutes for the cover film 54. It is contemplated that in other variations the test strip 26 can still include the cover film 54. Returning to the illustrated embodiment, all or part of the sterility sheet 24 of the lancet packet 44 can be treated and/or made to be hydrophilic so as to direct the fluid flow as well as enhance capillary action inside the capillary channel 48. Alternatively or additionally, it is envisioned that the sterility sheet 24 of the lancet packet 44 can have one or more hydrophobic sections that are used to direct fluid flow. With the lancet packet 44 disposed on the same side with the contacts 47, the interface between the LIT 56 and the meter can be simplified.

Figure 8:
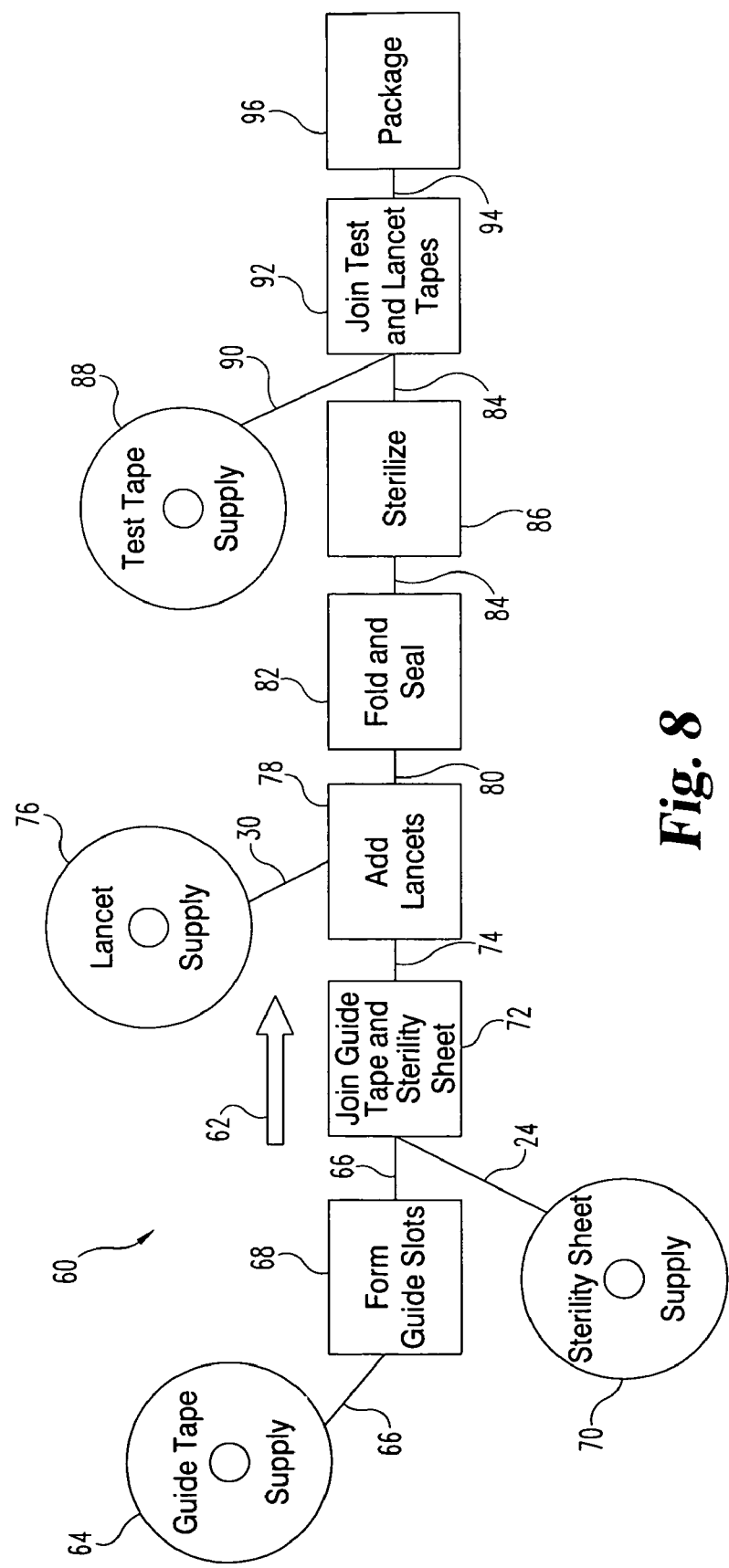
FIG. 8 is a diagram depicting a technique for mass producing the FIGS. 1 and 7 integrated disposables.

As mentioned above, it is desirable to inexpensively manufacture LITs in a manner that will not dramatically affect LIT sterility as well as the testing accuracy. A technique or method for mass producing LITs, such as the ones discussed above, as well as other types of integrated devices will now be described with reference to FIG. 8. FIG. 8 is a diagrammatic view of the various stages involved with mass-producing the LITs. Although diagram 60 in FIG. 8 illustrates a continuous process, it should recognized that in other embodiments one or more stages can be discrete or part of a discontinuous batch process. In the diagram 60 of FIG. 8, directional arrow 62 illustrates the general directional flow of the various manufacturing stages. It should be appreciated that selected stages can occur in a different order than is illustrated, and the equipment required to perform the various does not need to be oriented in the illustrated manner.

Figure 9:
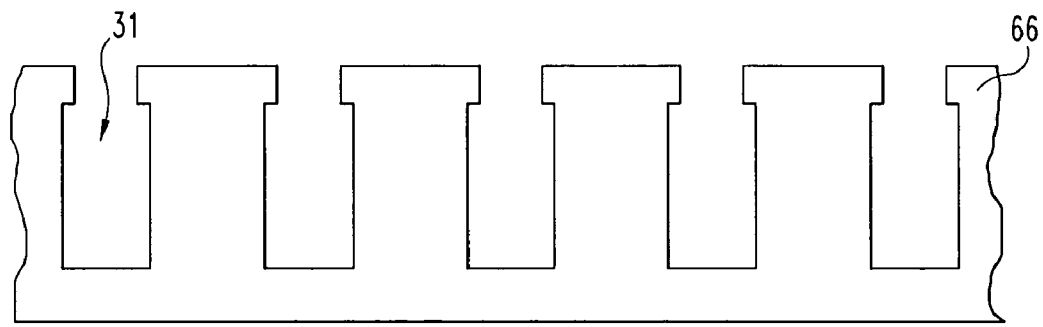
FIG. 9 is a top view of a guide tape formed during production of the FIGS. 1 and 7 integrated disposables.

Looking at FIG. 8, a guide tape supply 64 supplies a guide tape or spacer belt (web) 66 that is used to form the guide member 28 for the lancet assembly 22 (FIG. 1). In the illustrated embodiment, the guide tape supply 64 is in the form of a reel around which the guide tape 66 is wrapped, but it is contemplated that the guide tape 66 can be supplied in other manners, such as for example folded in a fanfold manner within a box. The guide tape 66 is well suited for mass producing LITs 20 in a continuous process. In stage 68, the guide slots 31 for the lancets 30 are formed in the guide tape 66, as is depicted in FIG. 9. The guide slots 31 can be formed in any number of manners, such as via punching, cutting, and/or etching, to name a few examples. In one embodiment, the guide tape 66 is made of one or more plastics, like vinyl polymers, polyimides, polyethylenes, polyesters, and styrenes. In one form, the guide tape 66 can be selected as a somewhat flexible polymeric material such as polyester, especially high temperature polyester materials; polyethylene naphthalate (PEN); and polyimide, or mixtures of two or more of these. Nevertheless, it should be recognized that the guide tape 66 as well as other components can be made from different materials, including metals as well as other plastics.

Figure 10:
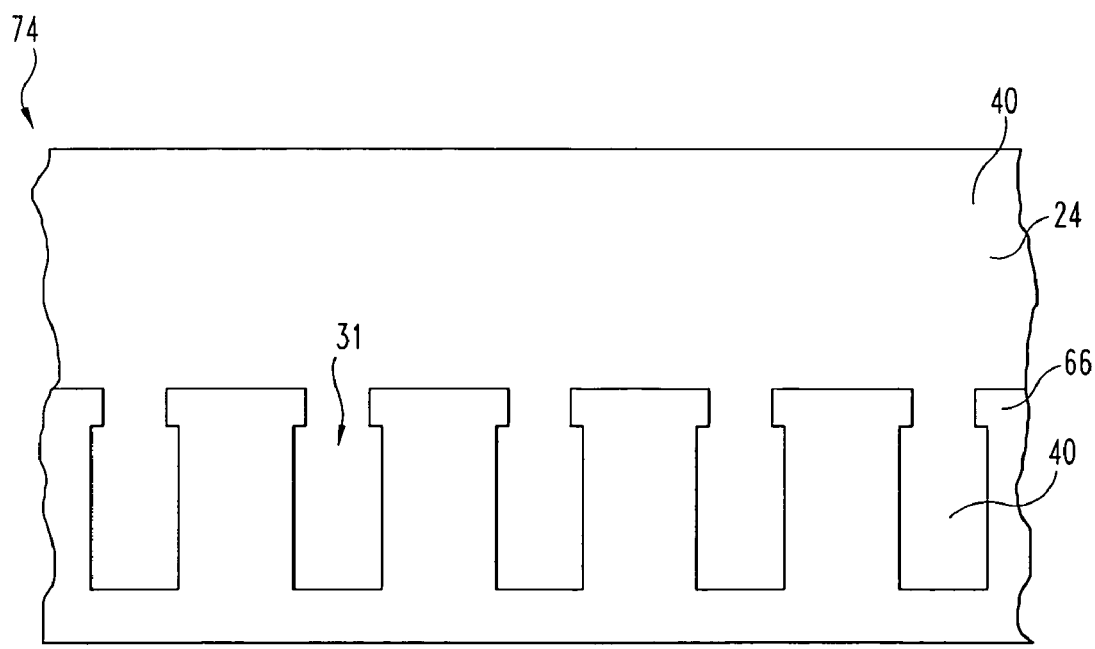
FIG. 10 is a top view of an intermediate sterility/guide tape formed during production of the FIGS. 1 and 7 integrated disposables.

A sterility sheet supply 70 supplies the sterility sheet 24 that is joined to the guide tape 66 in stage 72. The sterility sheet supply 70 in the depicted embodiment is in the form of a reel around which the sterility sheet 24 is wrapped, but it is contemplated that the sterility sheet supply 70 can be supplied in other manners, such as folded in a fanfold manner within a box. As can be seen in FIG. 10, one of the flaps 40 of the sterility sheet 24 in stage 72 is laminated to the bottom side of the guide tape 66, thereby enclosing one side of the guide slots 31. The sterility sheet 24 can be secured to the guide tape 66 in a number of manners. For example, the sterility sheet 24 in one embodiment is heat sealed to the guide tape 66, and in another embodiment, an adhesive is used. In the illustrated embodiment, the sterility sheet 24 is heat laminated with the guide tape 66 to create an intermediate sterility/guide tape (web) 74. In another embodiment, a laser can be used to seal the sterility sheet 24 with the guide tape 66. As mentioned before, the sterility sheet 24 or sections thereof can be hydrophobic or hydrophilic in order to direct the fluid flow from the incision. The sterility sheet 24 can be initially supplied in the sterility sheet supply 70 with hydrophobic/hydrophilic sections. The hydrophobic/hydrophilic sections can also be added before, during, or after the sterility sheet 24 is joined to the guide tape 66 in stage 72.

The guide tape 66 is made of a material that is compatible with the sterility sheet 24 for sealing the lancet assembly 22. In one form, the guide tape 66 and the sterility sheet 24 are biocompatible, have sufficient elongation strength, a substantially uniform thickness, and are stable with a selected sterilization process. The sterility sheet 24 is configured to seal with the guide tape 66, and the sterility sheet 24 is nonporous so as to maintain sterility of the lancet 30 in the lancet packet 44. Moreover, the sterility sheet 24 is constructed so as to prevent binding as the lancet 30 moves during lancing. The sterility sheet 24 needs to be sufficiently thick so as to prevent accidental ruptures of the sterility sheet 24, and at the same time, the sterility sheet 24 needs to be sufficiently thin enough so that the lancet 30 is able to consistently pierce the sterility sheet 24 during lancing without damaging the lancet tip 22. In one particular embodiment, the sterility sheet 24 has a thickness from about 10 to 100 μm. In one embodiment, the sterility sheet 24 is a sheet of metallic foil, and in another embodiment, the sterility sheet 24 is made of plastic. Various other materials can be suitable for creating the sterility sheet 24. For instance, the sterility sheet 24 can be made of polyethylene (low or high density), polypropylene, polyester, ethylene vinyl acetate, or some combination thereof, to name a few. In one example, the sterility sheet 24 is made of polyethylene. It nevertheless should be recognized that the sterility sheet 24 can be made of other types of materials.

As shown in Table 1, sterility sheet 24 can be made of various materials and thicknesses. These materials are available from suppliers such as Mitsubishi Films, Tredegar Film Products, AET Films, and DuPont Teijin Films, to name a few. In one embodiment, the sterility sheet 24 has material properties that enable it to form a seal with the guide member 28 that is strong, stable at elevated temperatures, immune to ultraviolet light or sunlight exposure, and compatible with a particular sterilization technique used on the lancet packet 44.

TABLE 1

| Type | Approximate Thickness (μm) |
| --- | --- |
| Polyethylene | 19.0-30.0 |
| Polyethylene/Low Density Polyethylene | 17.5-63.5 |
| Polypropylene | 23.0 |
| Polyester | 19.0 |
| Polyethylene/Ethylene Vinyl Acetate | 26.0 |

Both the sterility sheet 24 and guide member 28 need to be sufficiently strong so as to prevent accidental rupturing, but the sterility sheet 24 must still be pierceable by the lancet 30. In view of this, some of the desirable physical properties of the guide tape 66 and sterility sheet 24 are given below in Table 2.

TABLE 2

| Physical Properties | Sterility Sheet | Guide Member/Tape |
| --- | --- | --- |
| Elongation at break - MD | ≧110% | ≧150% |
| Elongation at break - TD | ≧100% | ≧120% |
| Tensile strength - MD | ≧138,000 KPa | ≧138,000 KPa |
| Tensile strength - TD | ≧138,000 KPa | ≧138,000 KPa |
| Thickness uniformity | ±10% | ±10% |

As alluded to above, both the sterility sheet 24 and the guide tape 66 generally need to be thermally robust or stable so as to not be damaged during manufacturing. For example, the sterility sheet 24 and guide tape 66 need to have the proper thermal properties that permit heat-sealing of the lancet packet, when used, but these components need to be also thermally stable enough to survive sterilization. Examples of some desirable thermal properties for the sterility sheet 24 and the guide tape 66 are provided below in Table 3.

TABLE 3

| Thermal Properties | Sterility Sheet | Guide Member/Tape |
| --- | --- | --- |
| Heat seal strength | >197 g/cm | >197 g/cm |
| Heat seal temperature | 135-190° C. | 135-190° C. |
| Shrinkage - MD | =4% | =2% |
| Shrinkage - TD | =2% | =2% |

Figure 11:
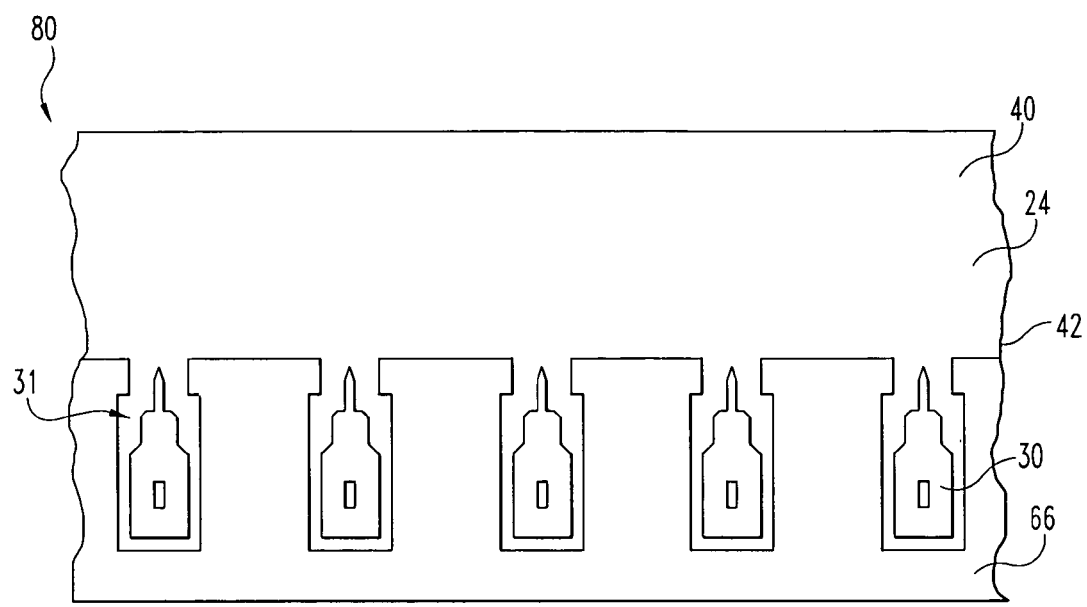
FIG. 11 is a top view of an unsealed packet tape formed during production of the FIGS. 1 and 7 integrated disposables.

Referring to FIGS. 8 and 11, a lancet supply 76 supplies the lancets 30 that are then deposited into the guide slots 31 in the guide tape 66 in stage 78 to form an unsealed packet tape (web) 80. In one embodiment, the lancets 30 are strung on a tape that is wrapped in a roll around a reel in the lancet supply 76, and before or after the lancets 30 are positioned in the guide slots 31, the lancets 30 are detached from the tape. In another embodiment, the lancets 30 are stored in a hopper, which then individually deposits the lancets 30 into the guide slots 31. As should be appreciated, the lancets 30 can be stored and supplied in other manners, as well. In one form, the lancets 30 are made at least in part of medical grade stainless steel, but it should be recognized that the lancets 30 can be made of other materials, such as ceramics and/or plastics. The lancet 30 in one particular embodiment is made of 304L or 17-7PH magnetized stainless steel in order to simplify handling, placement, and identification. When magnetized, the lancet 30 can be easily placed into the guide slots 31 via an electromagnet.

It is contemplated that stage 78 in FIG. 8 can be optional in other embodiments. For example, the guide tape 66 and lancet 30 in another embodiment are initially formed as a unitary structure in which the lancets 30 are attached via breakable tabs within the guide slot 31 in the guide tape 66. Photo-etching, die cutting, and/or stamping for example can be used to form the lancets 30 along with the guide slots 31 in the guide tape 66 before the sterility sheet 24 is even attached. It is also envisioned that stage 78 can occur before stage 72 in other embodiments, even when the lancets 30 and the guide tape 66 are formed as separate components. That is, the lancets 30 can be associated with the guide tape 66 before the sterility sheet 24 is attached to the guide tape 66.

Figure 12:
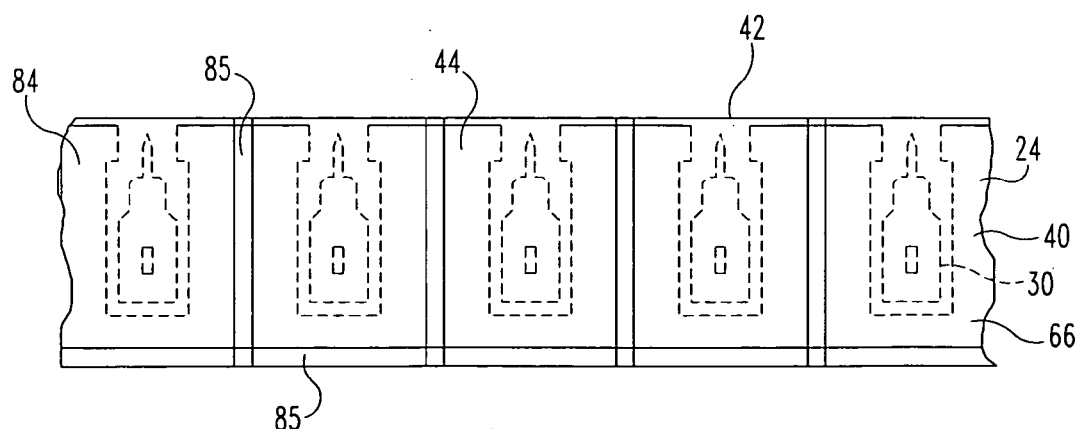
FIG. 12 is a top view of a sealed lancet packet tape formed during production of the FIGS. 1 and 7 integrated disposables.

In stage 82 (FIG. 8), the flap 40 of the sterility sheet 24 is folded at crease 42 around the guide tape 66 and then sealed with the guide tape 66 to form a sealed lancet packet tape (web) 84, as is depicted in FIG. 12. In one embodiment, the unsealed packet tape 80 is fed into a folding machine that folds the flap 40 of the sterility sheet 24 back onto the guide tape 66, and the unsealed packet tape 80 is then passed through heated rollers to laminate the sterility sheet 24 to the top of the guide tape 66, thereby creating the sealed tape packet 84. In another embodiment, a laser is used to laser seal the sterility sheet 24 with the guide tape 66. The folded flap 40 is sealed at seal lines or areas 85 to ensure a sterile barrier. It is desirable that the sealing technique in stage 82 does not obstruct or interfere with the movement of the lancet 30 by distorting the packet formed around the lancet 30. Moreover, it is desirable that the sealing technique does not alter the tensile properties of the sterility sheet 24 so that the lancet 30 is still able to consistently pierce the sterility sheet 24 during lancing. In view of this, it was discovered that the seal lines 85 between the individual lancets 30 can suitably include a fill seal, band seal, and/or joint seal, such as a compression, cut-through, or weld seal, to name a few examples. It should be recognized that the sterility sheet 24 can be sealed in other manners so long as the technique does not adversely affect seal integrity or the ability for the lancet 30 to lance an incision. Although folding and sealing have been described as a single step, it should be recognized that folding and sealing can occur in separate and distinct steps.

Instead of a single sterility sheet 24 that is folded around the guide tape 66, it is contemplated that in other embodiments two or more sterility sheets 24 can be sealed around the lancet 30 in stage 82. For instance, instead of folding the sterility sheet 24, two sterility sheets 24 can be joined together with the guide tape 66 and lancet 30 sandwiched in between. It is contemplated that the individual lancet packets 44 formed on the sealed tape 84 can be sealed in a high atmospheric pressure environment or pressurized in some other manner so that guide slots 31 of the lancet packet 44 are sealed to have a pressure higher than typical atmospheric pressure. With the higher pressure inside, the lancet packet 44 will tend to outgas when the sterility sheet 24 is punctured during lancing, thereby reducing the chance of contaminants being sucked onto the lancet 30 as the sterility sheet 24 is punctured. The pressurization of the lancet packets 44 additionally tends to reduce friction or interference between the lancets 30 and the sterility sheet 24 during lancing because the sterility sheet will tend to bulge outwardly, away from the lancet 30. It is also contemplated that the lancet packets 44 can be sealed to contain gases other than air and/or liquids, either in pressurized or unpressurized states. For example, the lancet packets 44 in other embodiments can be sealed in stage 82 to contain an antiseptic, like alcohol or phenol, and/or an anticoagulant. The antiseptic can be used to maintain the sterility of the lancet as well as to cleanse the wound created by the lancet 30. The anticoagulant can be used to promote bleeding from the incision formed by the lancet 30.

Referring to FIG. 8, after being sealed in stage 82, the sealed lancet packet tape 84 is then sterilized in stage 86. Sterilization in stage 86 can be accomplished by any number of sterilization methods, including: heat (e.g., dry or steam); ethylene oxide; radiation (e.g., gamma or electron beam); and plasma and/or light (e.g., infrared or ultraviolet), to name just a few examples. The optimal sterilization technique can depend on the design of the integrated disposable being sterilized as well as how the disposable is assembled. For example, the lancet 30, guide tape 66, and sterility sheet 24 in other embodiments can be individually sterilized using different sterilization techniques before being combined together in a sterile environment. Although the diagram 60 shows that the sterilization stage 86 occurs after the sealing stage 82, it should be appreciated that sterilization can occur during or before the sterility sheet 24 is sealed with the guide tape 66.

In stage 86, sterilization via radiation is a suitable process for sterilizing the sealed packet tape 84, since the process is dry, works at moderate temperatures, and has been validated by the United States Food and Drug Administration (FDA). Gamma radiation can penetrate deeply into the lancet tape 84 to sterilize the lancet 30. Gamma radiation induces breaks in the DNA so as to prevent replication of any pathogens, thereby sterilizing the lancet 30. Industrial gamma radiation facilities typically have a closeable shielded room into which totes of lancet packets 44 to be sterilized are placed. The totes are continuously fed, such as on a trolley, through a chamber in the shielded room that is exposed to the gamma radiation. In one embodiment, a cobalt source, such as cobalt 60, is used to sterilize the lancet tapes 84. However, it is contemplated that other radioactive material can be used to sterilize the lancet tapes 84. Sterilization takes place with no residual radiation in the lancet tapes 84. Radiation indicators can be placed inside the lancet tape 84 to measure the dosage of radiation.

However, it has been found that gamma radiation sterilization can have some significant drawbacks. For instance, due to the health dangers associated with radiation exposure, gamma radiation sterilization requires specialized facilities, and gamma radiation sterilization is typically done to an end package as a final step prior to shipment. Gamma radiation treatment also typically requires long exposure times, and there is some consumer sentiment against the potential health concerns created by exposing products to radiation.

On the other hand, electron beam (E-beam) radiation typically can be targeted, requires shorter exposure times, and does not induce radioactivity in any material. E-beam sterilization is that branch of radiation processing where the changes are induced by use of accelerated electrons as the ionizing radiation source of the process. E-beam sterilization uses ionizing energy in the form of accelerated electrons. Ionization is lethal to all forms of life when a sufficient dose is absorbed. During ionization of a target object, atomic electrons are removed from molecules, thereby breaking molecular bonds in materials or damaging the DNA of potentially harmful pathogens. For integrated disposables, such as the LITs 20, 56 described herein, it has been discovered that E-beam sterilization is the favored sterilization technique because E-beam sterilization can be easily incorporated into batch or in-line/reel-to-reel manufacturing processes, such as the one described herein. In addition, E-beam sterilization usually allows for localized sterilization through shielding or energy control. It should be noted that an E-beam sterilization technique according to one embodiment will be later described in detail below starting with reference to FIG. 14.

With reference to FIG. 8, a test tape supply 88 supplies a test tape or belt 90 that includes a plurality of the test strips 26. In the illustrated embodiment, the test tape supply 88 is in the form of a reel around which the test tape 90 is wrapped, but it is contemplated that the test tape 90 can be supplied in other manners, such as for example folded within a box or dispensed from a hopper. Nevertheless, it should be recognized that having the test strips 26 joined together in the test tape 90 simplifies manufacturing for mass production of the LITs 20. In the illustrated embodiment, the test tape 90 is in the form of a continuous belt, and in another embodiment, the test tape 90 can be a belt that joins discrete test strips 26 together.

Figure 13:
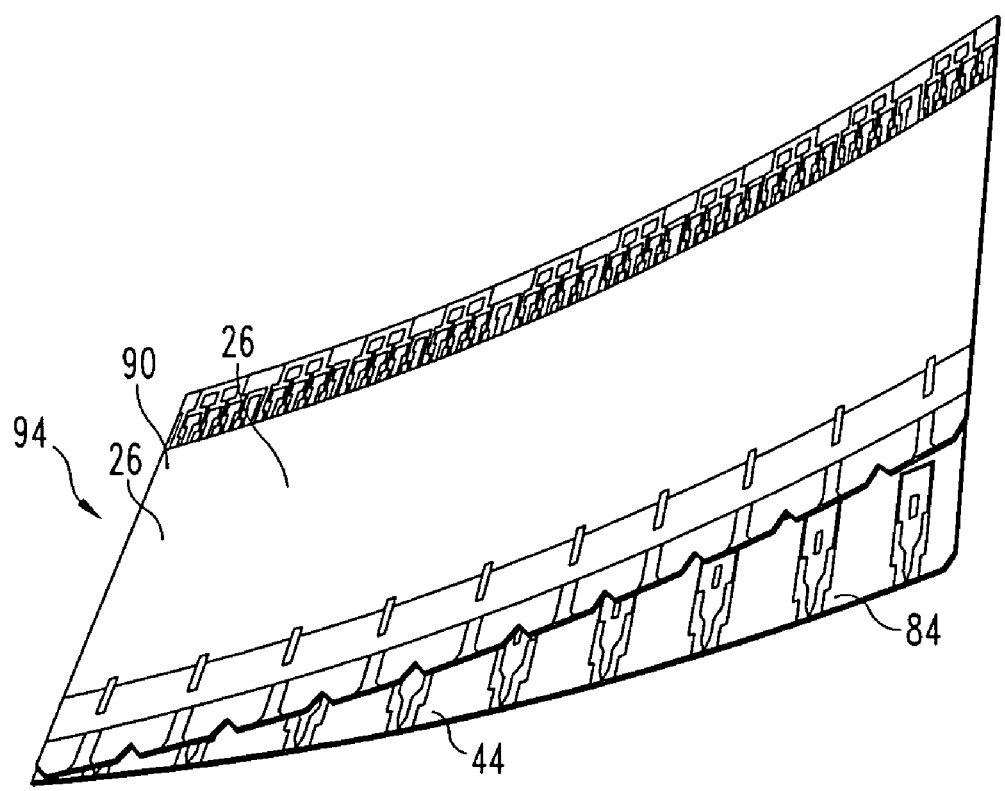
FIG. 13 is a perspective view of a test tape being joined to the FIG. 12 sealed lancet packet tape during production of the FIG. 1 integrated disposable.

After the sealed lancet packet tape 84 is sterilized in stage 86, the test tape 90 is joined with the sealed lancet packet tape 84 in stage 92 to form an LIT tape or belt 94, as is depicted in FIGS. 8 and 13. As noted before, only the lancet 30 needs to be sterilized because the lancet 30 punctures the skin, while the rest of the components, which do not enter the skin, do not need to be sterilized. Joining the test strip tape 90 after the lancet packet tape 84 has been sterilized avoids a number of significant issues. As mentioned before, the sterilization process, such as occurs in stage 86, can be detrimental to biosensors used in integrated disposables, such as the above-described LITs 20, 56. In particular, the chemical reagents within the test strip 26 can be damaged or degraded by the sterilization process. For example, not only does the ionization created by an E-beam sterilization process destroy harmful pathogens, the ionization also destroys or degrades the enzymes in the reagent that are used to test the fluid sample. In addition, the plastics, adhesives, and/or other materials used to manufacture the integrated disposables can be adversely affected by the sterilization process as well. Packaging and maintaining sterility of the integrated disposable can also be problematic. Cross contamination of chemicals from the test strip 26 onto the lancet 30 can occur if an integrated disposable is sterilized after the lancet 30 is attached to the test strip 26. Again, the technique illustrated in FIG. 8 resolves these issues along with other issues because the lancets 30 are separately enclosed and sterilized in the sealed lancet packet tape 84 before being joined to the test strip tape 90 in stage 92. In one example, the lancet packet tape 84 is secured to the test tape 90 with an adhesive. In another example, the lancet packet tape 84 is laminated with the test tape 90 and then heat-sealed together. It nevertheless should be recognized that the tapes 84, 90 can be joined together in other manners.

Once assembled in stage 92, the LIT tape 94 can then be packaged in stage 96. The LIT tape 94 in stage 96 can be packaged as a continuous tape or segmented into individual LITs 20. For instance, the LIT tape 94 can be packaged into multi-use cassettes, cartridges, drums, and the like in stage 96. In another example, individual LITs 20 can be cut from the LIT tape 94 to form individual disposables. The LIT tape 94 in this example is cut along the seal lines 85 (FIG. 12) so that the integrity of the seal is maintained. It should be recognized that the above-described techniques provide an efficient and practical way for mass producing integrated disposables, such as the LITs 20, 56 described above.

As mentioned before, the guide member 28 can be an optional component of the LIT 20. It should be recognized that the previously described techniques and systems can be readily modified to produce LITs 20 without guide members 28. For example, the technique and system illustrated in FIG. 8 can be modified to eliminate the guide tape supply 64 as well as stages 68 (forming guide slots) and 72 (joining guide tape to sterility sheet). FIGS. 14 and 15 show web and single views of a packet assembly 98 having only the lancet 30 enclosed (no guide member). The seal lines 85 around the lancets 30 are sized and positioned to guide the lancets 30 during lancing. The seal lines 85 in FIGS. 14 and 15 are continuous seals to ensure that the lancets 30 are completely sealed from the environment. To allow sufficient area for singulation (e.g., cutting or otherwise separating) of the individual units, the seal lines 85 are in the form of a wide single seal line or double seal lines. It should be recognized that other seal patterns can be used as well in other embodiments. For example, the seal lines 85 can include one, two, three or more seal lines. The sterility sheet 24 in one example is folded over and sealed to form the packet. In other examples, two or more sterility sheets 24 can be sealed together to enclose the lancet 30 inside the packet. In FIGS. 14 and 15, the package assembly has a seal edge 100 that is slightly curved between the seal lines 85, but the seal edge 100 can be shaped differently in other embodiments.

FIG. 16 shows an enlarged view of the rectangular area identified by reference numeral 16 in FIG. 14. In particular, FIG. 16 shows an enlarged view of the interface of the fold line 42, seal line 85 and seal edge 100. It was discovered that a small channel would form along the fold line 42 that would create a leakage problem when the individual lancet packets were separated or singulated from one another. FIGS. 16-18 illustrate embodiments of seals that generally close or plug this channel by melting the sheet 24 across the seal edge 100, generally at the seal line 85. In FIG. 16, a seal arrangement comprising a pressed seal is provided by compressing a hot horn or anvil across the seal edge 100. In particular, the seal edge 100 at the seal line 85 has an arced section 102 in FIG. 16 that reduces the risk of leakage when the packet is cut or otherwise singulated at the seal line 85. As shown, the pattern of the seal edge 100 in FIG. 16 has an overall scalloped shape but can have whatever shape provided by the hot horn or anvil to effectively seal the open channel across the edge 100. As illustrated in FIG. 17, a notch 104 is provided at the end of the seal line 85 along the seal edge 100 by applying a hot knife thereacross. Likewise, a grid patch 106 at the end of the seal line 85 minimized leakage, as is shown in FIG. 18, may be provided by ultrasonic welding. The grid patch 106 in FIG. 18 additionally is found to provide additional reinforcement to the seal line 85. As should be appreciated, these various seal patterns can be formed at any appropriate stage of manufacture, including at high speeds such as the reel-to-reel continuous process shown in FIG. 8, e.g., during the fold and seal stage 82, and/or at other times, such as when the LITs 20 are singulated.

As mentioned before when discussing the sterilization stage 86 in FIG. 8, it has been found that E-beam sterilization is a favored sterilization technique for integrated disposables, such as the LITs 20, 56, because E-beam sterilization can be easily incorporated into batch or in-line/reel-to-reel manufacturing processes. In addition, E-beam sterilization usually allows for localized sterilization through shielding or energy control. E-beam sterilization generally involves the deposition of energy via electrons into a product, from a directional, controllable, on-off source of energy. This deposited energy creates free radical action, which in turn creates chemical changes within that product. As with any electrical equipment, the electron accelerators can be shut down at any time. When the accelerator used for E-beam sterilization is off, it is completely safe to enter the irradiation area and work anywhere near the equipment to perform scheduled or unscheduled maintenance, which is beneficial in a mass-production environment. Given that no radioactive material is involved in the E-beam sterilization process, there are no issues associated with handling, licensing, shipping, disposal, and/or use of radioactive materials.

Figure 19:
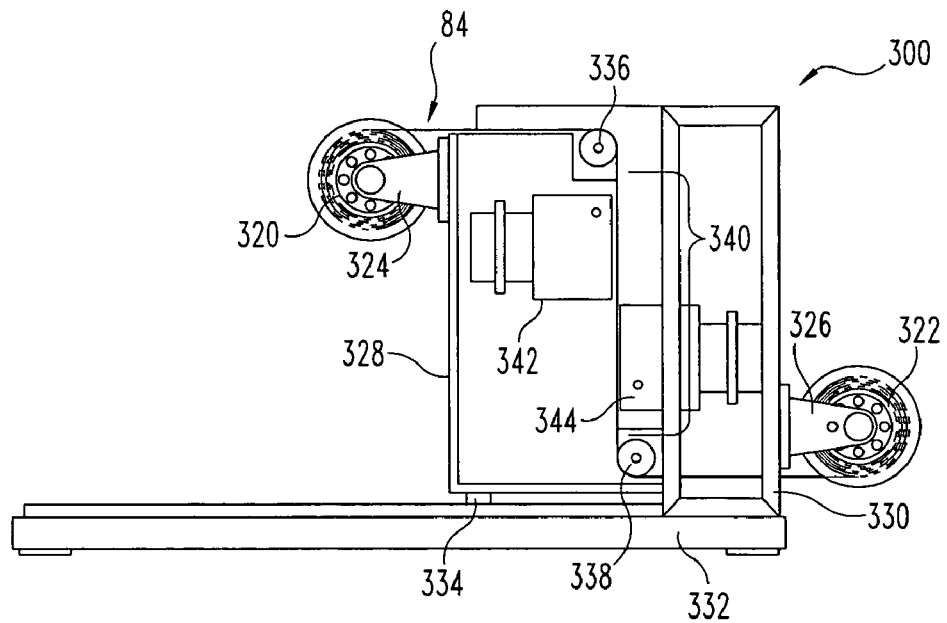
FIG. 19 shows a side view of an electron beam radiation system in an operating position for sterilizing the FIG. 12 sealed lancet packet in accordance with one embodiment.
Figure 20:
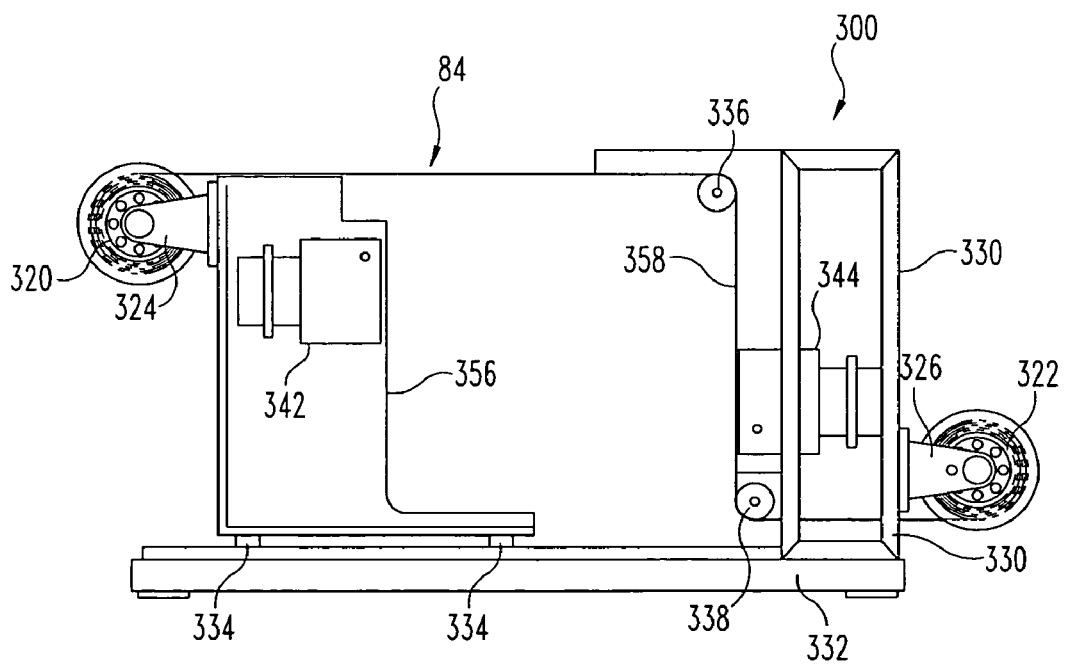
FIG. 20 shows a side view of the FIG. 19 system in an open position for access to components of the system.
Figure 21:
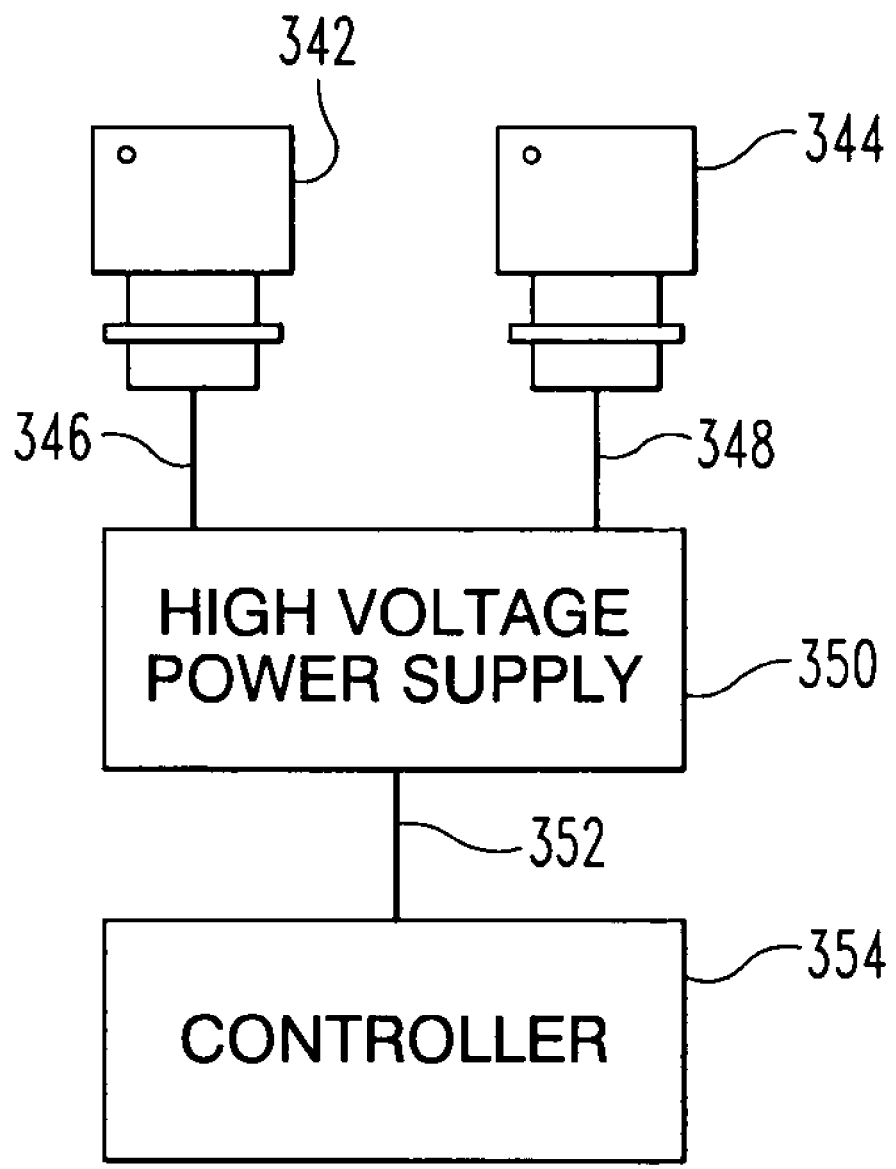
FIG. 21 is a schematic drawing showing the electrical interconnection for the electron beam radiation system of FIG. 19.

FIGS. 19, 20, and 21 illustrate an electron beam (E-beam) system 300 for sterilizing the sealed lancet packet tape 84. Considering that the sterilized location can be tightly controlled with E-beam sterilization, in a continuous process as shown in FIG. 8, a portion or the entire lancet assembly 22 can be sterilized through the sterility sheet 24 using the E-beam system 300. Although E-beam system 300 will be described with reference to a continuous process in which the lancet tape 84 is sterilized, it should be recognize that a single lancet packet 44 or a batch of singulated packets 44 can be sterilized with the E-beam system 300 of FIG. 19 or with other types of E-beam devices.

Referring specifically to FIG. 19, the sealed lancet packet tape 84 extends between a pair of rollers 320 and 322. Depending upon the direction of movement of the lancet packet tape 84, one of the rollers 320, 322 is the supply and the other is the take-up. When the E-beam system 300 is incorporated into a continuous process, such as illustrated in FIG. 8, the rollers 320, 322 can be eliminated. The rollers 320 and 322 are journaled in supports 324 and 326, respectively. Support 324 is connected to frame 328 and support 326 is connected to frame 330. Motors for driving the rollers 320 and 322 are not shown to simplify the understanding of the invention. It should be apparent, however, to those skilled in the art, that the rollers 320 and 322 are rotated to displace the lancet packet tape 84 at substantially continuous velocities that will be described later. In addition, the rollers 320 and 322 are rotated relative to one another in a way that maintains proper tension in the lancet packet tape 84.

The frame 330 is fixed to a base 332. The frame 328 is displaceably mounted on base 332 between the operating position of FIG. 19 and access position of FIG. 20 by means of guides 334. The access position of FIG. 20 enables replacement and repair of the components. A pair of guide rollers 336 and 338 are journaled on frame 330 through an appropriate connection (not shown) to lancet packet tape 84 in a direction substantially perpendicular to its path when entering or exiting rollers 320, 322. The path between guide rollers 336 and 338 is referred to as a target location 340 through which the lancet packet tape 84 is subjected to electron beam radiation from a pair of electron beam radiation emitter devices 342 and 344. In another embodiment described below, only one of either devices 342 or 344 is used to sterilize the tape 84.

E-beam radiation emitter devices or horns 342 and 344 are for example widely employed to sterilize medical devices, pasteurize food, disinfect consumer products, modify material properties, and sanitize post office mail. The electron beam emitters 342, 344 generate electrons in a vacuum environment and accelerate them to over half the speed the light, allowing the electrons to exit the vacuum chamber through a thin electron permeable membrane. The electrons are generated by passing electrical currents through a thin tungsten filament. The tungsten element heats up due to electrical resistance and electrons boil on the surface. A high voltage plate, typically located behind the tungsten filament, creates a negative electric field. The electrons on the surface of the hot tungsten filament are negatively charged and are therefore repelled by the electric field. The electrons are accelerated directly away from both the high voltage metal plate and the filament. The electrons continue to accelerate as they travel the length of the vacuum chamber until they reach the electron permeable membrane. The electrons at this high energy level are able to pass directly through a six micron thick membrane because of its low density. These electrons are now free in the atmosphere and are able to be used for sterilization.

The electrical and electronic components necessary to operate the electron beam radiation devices 342 and 344 are shown in FIG. 21. The electron beam emitter devices 342 and 344 have high voltage cables 346 and 348, respectively, which extend from a high voltage power supply 350. Power supply 350 is activated through a cable 352 from a controller 354. The output of the electron beam devices 342 and 344 is generally expressed either in kiloelectron volts (keV) or millielectron volts (meV). Millielectron volts are considered to be high power electron beam radiation devices; whereas it has been found low level electron beam radiation devices on the order of keV may be employed in the E-beam system 300 of FIG. 19. In one embodiment, the electron beam radiation devices 342, 344 have outputs of up to two-hundred kiloelectron volts (200 keV), and in one particular embodiment, the electron beam radiation devices 342, 344 emit during sterilization one hundred and fifty kiloelectron volts (150 keV) at 5 milliampere (5 mA).

Figure 22:
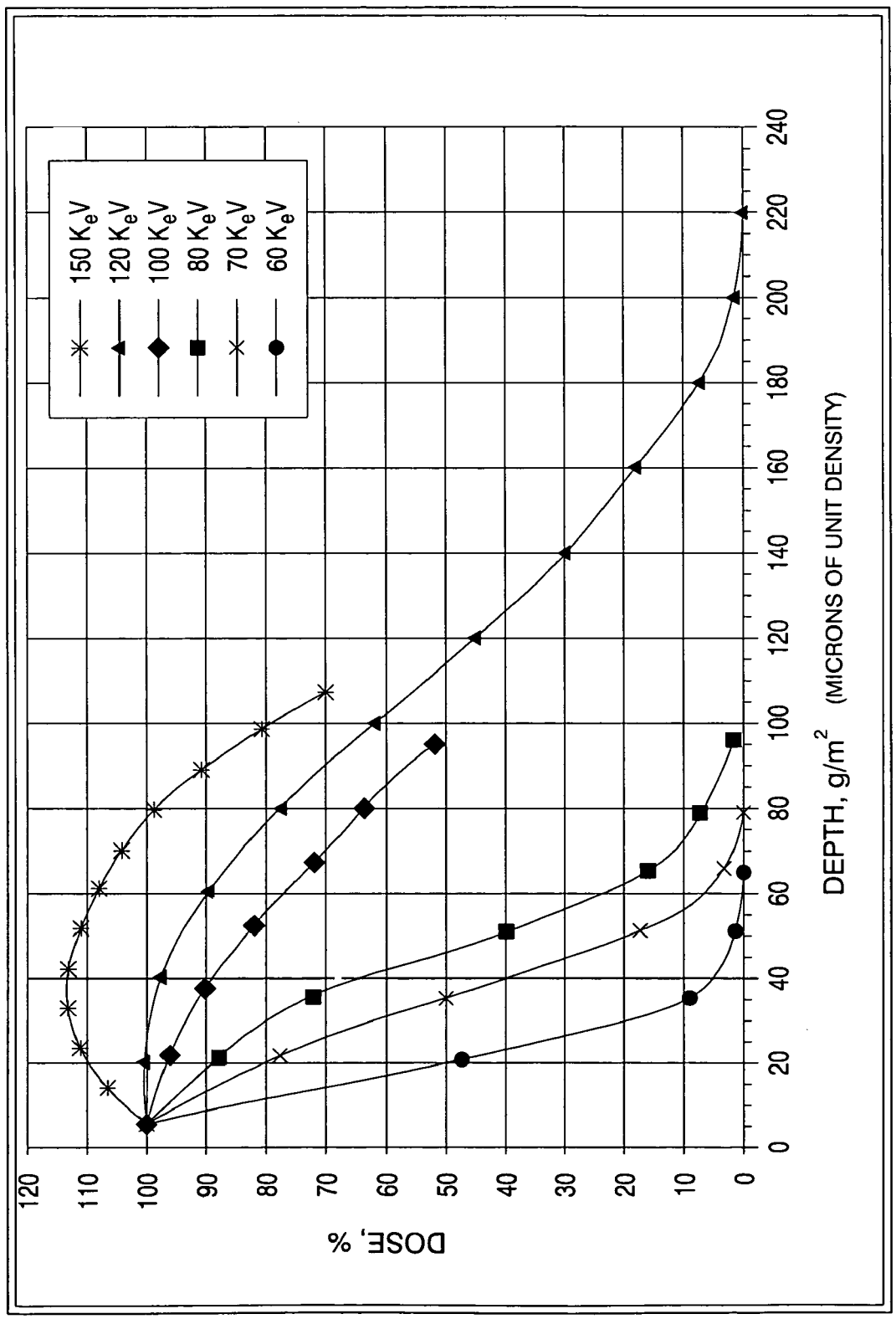
FIG. 22 shows a graph illustrating an electron beam depth-dose curves at various potentials.

Depending on the voltage applied, the depth to which the E-beam system 300 can sterilize material can be limited. FIG. 22 provides multiple depth-dose curves for various voltages. The vertical axis of the graph in FIG. 22 represents the dose percentage, and the horizontal axis represents the depth of the material being sterilized. As can be seen, the effective penetration depth of the sterilizing E-beam generally increases as a greater potential is applied. However, for a given E-beam system 300, the applied potential can be only increased so much to a point until a higher powered electron accelerator is required. The higher powered electron accelerators are usually more expensive to purchase and maintain. Further complicating matters is that the high powered electron accelerators are usually not as well suited for high production volumes in comparison to their lower powered counterparts.

Figure 23:
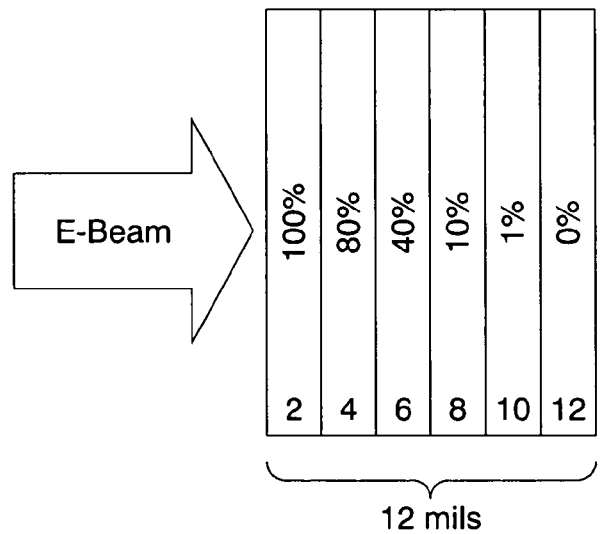
FIG. 23 illustrates sterilization effectiveness as a function of depth for single-sided irradiation of a lancet material with a twelve mil (0.012 inch) thickness by a 150 keV electron beam.

FIG. 23 illustrates the effect shown in FIG. 22 in another way. Specifically, FIG. 23 illustrates the dose effectiveness when one hundred and fifty kiloelectron volts (150 keV) E-beam is applied to only one side of a 12 mil (0.012 inches) thick lancet packet tape 84. It should be recognized that, when only applied to one side, the E-beam is marginally effective for at most half the thickness of the lancet packet tape 84. It can be seen that beyond six mil (0.006 inches) depth the radiation dose unacceptably drops to near zero. One solution to address this issue is to increase the energy applied to the lancet packet tape 84. However, as explained before, the amount of applied energy is limited based on the operational limits for a given electron accelerator. As a result, the applied energy can only be increased so far until a more expensive accelerator is required, which is typically less suited for high production volumes.

Figure 24:
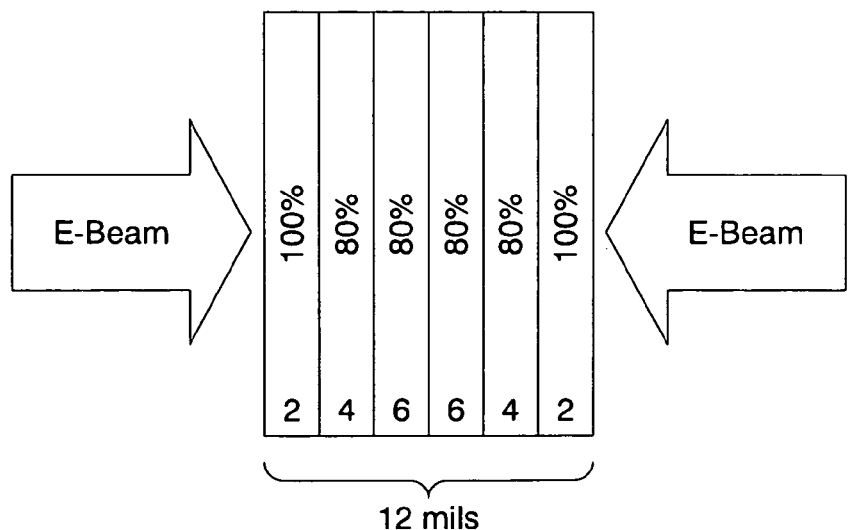
FIG. 24 illustrates sterilization effectiveness as a function of depth for two-sided irradiation of a lancet material with a twelve mil (0.012 inch) thickness by a 150 keV electron beam.

It, however, was discovered that the sterilization effectiveness of E-beam radiation significantly improves when an electron beam is applied to both sides of the material being sterilized. In contrast to the FIG. 23 example where single-sided irradiation is used, when electron beams are applied on both sides (two-sided irradiation) of the lancet packet tape 84 having a thickness of 12 mil (0.012 inches), as is depicted in FIG. 24, beam penetration of the inner-most portion of the element drops to no less than eighty percent (80%). Thus, by applying two-sided irradiation, sterilization is enhanced without the need to increase the applied energy. The lower energy requirements in turn permit the use of lower powered electron accelerators, which are more practical for high production environments.

Returning to FIGS. 19 and 20, the electron beam radiation devices 342, 344 are positioned on opposite faces of the lancet packet tape 84 so that two-sided irradiation can occur. The electron beam radiation devices 342, 344 are also adjacent one another so that the radiation beams are near one another. In one form, the electron beam devices 342, 344 are powerful enough to emit a pattern of radiation approximately over a 20 inch by 4 inch area to sterilize the lancet tape 84. Depending on the E-beam sterilization equipment used, these dimensions can of course be different. In the illustrated embodiment, operator safety is maintained by placement of a first L shaped shield 356 on frame 328 and a second L shaped shield 358 on frame 330 to effectively shield an operator when the electron beam radiation devices are operating in the target location 340.

The lancet packet tape 84 is displaced between the rollers 320, 322 while the electron beam devices 342, 344 irradiate opposite faces of the tape 84 with approximately one hundred and fifty kiloelectron volts (150 keV). This enables rapid sterilization of the lancet packet tape 84 and allows for tape velocities of up to one hundred meters per minute. It should be recognized that the resultant sterilization process is extremely economical and effective. The sterilization system 300 is compact and can be easily integrated into a production line. Replacement of the hardware is rapid so that it has minimal impact on processing time and rates. No special electron beam experience is required by the operator since the components are self-contained and the radiation devices do not require active vacuum pumping.

In another embodiment, only one of the emitters 342, 344 is used to emit a pattern of radiation. For purposes of illustration only, emitter 342 will emit an electron beam, while the other emitter 344 will be inactive. In one form, the pattern of radiation is over an area of approximately 10 inches by 4 inches to sterilize one side of the lancet tape 84, but again, these dimensions can vary in other systems. The lancet packet tape 84 is displaced between the rollers 320, 322 while the device 342 emits radiation along one side of the lancet tape 84. After the first side of the lancet tape 84 is sterilized, the tape 84 is again displaced between the rollers 320, 322 such that the opposite side of the lancet packet tape 84 is radiated and sterilized. To irradiate the other side, the lancet packet tape 84 can be flipped or the other emitter 344 can be activated to irradiate the other side during the second pass.

While the E-beam system 300 illustrated in the drawings has two emitters 342, 344, the system 300 in other embodiments can have a single emitter that is able to irradiate a single side of the lancet packet tape 84 at a time. An example of an E-beam sterilization device that can be used for one-sided sterilization includes an Alis brand medium-energy, high-power industrial electron accelerator unit produced by the IBA Group of Louvain-la-Neuve, Belgium. Again, to irradiate both sides when a single emitter is used, the lancet packet tape 84 can be flipped between two passes by the single emitter. It is contemplated that both sides of the lancet packet tape 84 can be irradiated in other manners. For example, the tape 84 in other embodiments can be threaded through rollers such that both sides are irradiated in a single pass by the emitter.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents and patent applications cited in this specification are herein incorporated by reference as if each individual publication, patent or patent application was specifically and individually indicated to be incorporated by reference as set forth in its entirety herein.

What is claimed is:

1. A method of manufacturing a tape of integrated disposables, comprising: forming guide slots in a web of lancets, wherein the guide slots provide a slot opening at one edge of the web; attaching a sterility sheet to the web to cover one side of the guide slots; depositing the lancets in the guide slots; enclosing the guide slots with the lancets therein by folding the sterility sheet around the edge of the web;
    sealing the web of lancets within a sterility sheet;
    sterilizing the lancets; wherein said sterilizing includes exposing the lancets to one or more electron beams directed through the sterility sheet and
    joining the web of the lancets with a belt that has a plurality of biosensors after said sterilizing to create the tape of integrated disposables.

2. The method of claim 1, wherein said sealing the web includes sealing between the lancets to form individual lancet packets.

3. The method of claim 2, further comprising:
    separating the integrated disposables from the tape after said joining.

4. The method of claim 3, wherein said separating includes cutting the integrated disposables from the tape.

5. The method of claim 1, wherein said sealing includes heat laminating the sterility sheet to the web.

6. The method of claim 1, wherein said sealing includes laser sealing the sterility sheet with the web.

7. The method of claim 1, wherein said exposing includes irradiating opposing sides of the lancets through the sterility sheet.

8. The method of claim 1, wherein said sterilizing the lancets includes exposing the lancets to sterilizing chemicals prior to said sealing the web of the lancets within the sterility sheet.

9. The method of claim 1, wherein said sterilizing includes exposing the lancets to radiation directed through the sterility sheet.

10. The method of claim 1, wherein said sterilizing the lancets occurs after said sealing.

11. The method of claim 1, wherein said joining includes adhering with an adhesive the web of the lancets to the belt of the biosensors.

12. The method of claim 1, wherein said sealing includes:
    forming seal lines that are configured to guide the lancets during lancing without the need for a separate guide member.

13. The method of claim 1, wherein said sealing the web includes:
    folding the sterility sheet around the web to form a fold line;
    creating a seal edge along the fold line;
    forming seal lines between the lancets with arched sections along the seal edge; and
    cutting along the seal lines to separate the lancets.

14. The method of claim 1, wherein said sealing the web includes:
    folding the sterility sheet around the web to form a fold line;
    creating a seal edge along the fold line;
    forming seal lines between the lancets with notches at the seal edge; and
    cutting along the seal lines to separate the lancets.

15. The method of claim 1, wherein said sealing the web includes:
    folding the sterility sheet around the web to form a fold line;
    creating a seal edge along the fold line;
    forming seal lines between the lancets with grid patches at the seal edge; and
    cutting along the seal lines to separate the lancets.

16. The method of claim 1, wherein said sealing, said sterilizing, and said joining occur in a continuous process.

17. The method of claim 1, wherein said sealing, said sterilizing, and said joining occur in a discontinuous batch process.

18. The method of claim 1, wherein said sealing includes sealing two or more sheets together to form the sterility sheet.

19. The method of claim 1, further comprising:
    folding the sterility sheet around the web to form a fold line;
    creating a seal edge along the fold line;
    forming seal lines between the lancets;
    melting the sterility sheet across the seal edge at the seal lines to minimize leakage; and
    cutting along the seal lines to separate the lancets.

20. A method of manufacturing a tape of integrated disposables, comprising: forming guide slots in a web of lancets, wherein the guide slots provide a slot opening at one edge of the web; attaching a sterility sheet to the web to cover one side of the guide slots; depositing the lancets in the guide slots; enclosing the guide slots with the lancet therein by folding the sterility sheet around the edge of the web;
    creating the lancet packet tape by sealing a plurality of lancets within the sterility sheet; wherein said creating the lancet packet tape includes sealing the lancets within the sterility sheet at a pressure higher than typical atmospheric pressure
    wherein said creating the lancet packet tape includes forming a seal between each of the lancets to form distinguishable lancet packets;
    attaching the lancet packet tape to a biosensor tape that includes a plurality of biosensors; and
    sterilizing the lancet packet tape before said attaching the lancet packet tape to the biosensor tape.

21. The method of claim 20, wherein said attaching includes aligning the lancet packets with the biosensors to form distinct integrated disposables as part of an integrated disposable tape.

22. The method of claim 21, further comprising detaching the integrated disposables from the integrated disposable tape.

23. The method of claim 21, further comprising packaging the integrated disposable tape inside a cassette.

24. The method of claim 20, wherein said sterilizing includes irradiating opposing sides of the lancet packet tape with electrons.

25. The method of claim 20, wherein said creating the lancet packet tape includes:
   creating guides slots within a guide tape;
   depositing the lancets in the guide slots; and
   enclosing the guide slots by sealing the sterility sheet to the guide tape.

26. The method of claim 20, wherein said creating the lancet packet tape includes sealing an antiseptic inside the lancet packets.

27. The method of claim 20, wherein said creating the lancet packet tape includes sealing an anticoagulant inside the lancet packets.

28. The method of claim 20, wherein said creating, said attaching, and said sterilizing occur in a continuous process.

29. The method of claim 20, wherein said creating, said attaching, and said sterilizing occur in a discontinuous batch process.

30. The method of claim 20, wherein said creating includes sealing two or more sheets together to form the lancet packet.

31. A method of manufacturing a tape of integrated disposables, comprising: forming guide slots in a web of lancets, wherein the guide slots provide a slot opening at one edge of the web; attaching a sterility sheet to the web to cover one side of the guide slots; depositing the lancets in the guide slots; enclosing the guide slots with the lancet therein by folding the sterility sheet around the edge of the web to form;
   a lancet tape, wherein the lancet tape has opposing first and second sides;
   sterilizing the lancet tape with an electron beam sterilization system, wherein said sterilizing includes exposing the lancets to one or more electron beams directed through the sterility sheet wherein said sterilizing the lancet tape includes
      irradiating the first side of the lancet tape with one or more first electron beams, and
      irradiating the second side of the lancet tape with one or more second electron beams;
   sealing the lancet tape within the sterility sheet before said sterilizing; and
   attaching a biosensor tape to the lancet tape after said sterilizing to create an integrated disposable tape.

32. The method of claim 31, wherein:
the electron beam sterilization system includes a first emitter that emits the first electron beam and a second emitter that emits the second electron beam;
the first emitter faces the first side of the lancet tape;
the second emitter faces the second side of the lancet tape; and
said sterilizing includes feeding the lancet tape between the first emitter and the second emitter to sterilize the lancet tape in a single pass.

33. The method of claim 31, wherein:
the electron beam sterilization system includes an electron emitter;
said irradiating the first side of the lancet tape includes passing the lancet tape by the emitter with the first side of the lancet tape facing the emitter; and
said irradiating the second side of the lancet tape includes passing the lancet tape by the emitter with the second side of the lancet tape facing the emitter.

* * * * *